United States Patent
Pallas et al.

(10) Patent No.: US 11,590,506 B2
(45) Date of Patent: *Feb. 28, 2023

(54) SYSTEMS AND METHODS FOR BIOLOGICAL ANALYSIS

(71) Applicant: LIFE TECHNOLOGIES CORPORATION, Carlsbad, CA (US)

(72) Inventors: Michael C. Pallas, San Bruno, CA (US); James C. Nurse, Sequim, WA (US); Gary Lim, San Francisco, CA (US); Theodore E. Straub, Lexington, MA (US); Eliodor Ghenciu, Atherton, CA (US); Evan Foster, San Mateo, CA (US); Jorge Fonseca, East Palo Alto, CA (US); Kevin Maher, Woodside, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 16/426,631

(22) Filed: May 30, 2019

(65) Prior Publication Data

US 2019/0381502 A1    Dec. 19, 2019

Related U.S. Application Data

(62) Division of application No. 14/385,730, filed as application No. PCT/US2013/032420 on Mar. 15, 2013, now abandoned.

(Continued)

(51) Int. Cl.
*B01L 3/00* (2006.01)
*C12Q 1/6806* (2018.01)

(Continued)

(52) U.S. Cl.
CPC ............. *B01L 3/50857* (2013.01); *B01L 3/50* (2013.01); *B01L 3/50851* (2013.01);
(Continued)

(58) Field of Classification Search
CPC ............ C12Q 1/6837; C12Q 2535/122; B01L 2300/0829; B01L 2300/0819;
(Continued)

(56) References Cited

U.S. PATENT DOCUMENTS 10,627,420 B2 * 4/2020 Pallas ................. B01J 19/0046
2002/0164820 A1 * 11/2002 Brown ................. B01L 3/5088
436/180

(Continued)

FOREIGN PATENT DOCUMENTS

CN    1861800 A    11/2006
EP    1693337 A1    8/2006

(Continued)

OTHER PUBLICATIONS

Hatch, Andrew C. et al., "1-Million Droplet Array with Wide-Field Fluorescence Imaging for Digital PCR", Lab on a Chip. vol. 11, No. 22, 2011, p. 3838-3845.

(Continued)

*Primary Examiner* — Matthew D Krcha

(57) ABSTRACT

A system for performing biological reactions is provided. The system includes a chip including a substrate and a plurality of reaction sites. The plurality of reaction sites are each configured to include a liquid sample of at most one nanoliter. Further, the system includes a control system configured to initiate biological reactions within the liquid samples. The system further includes a detection system configured to detect biological reactions on the chip. According to various embodiments, the chip includes at (Continued)

least 20000 reaction sites. In other embodiments, the chip includes at least 30000 reaction sites.

21 Claims, 20 Drawing Sheets

Related U.S. Application Data

(60) Provisional application No. 61/774,499, filed on Mar. 7, 2013, provisional application No. 61/723,658, filed on Nov. 7, 2012, provisional application No. 61/723,759, filed on Nov. 7, 2012, provisional application No. 61/723,738, filed on Nov. 7, 2012, provisional application No. 61/723,710, filed on Nov. 7, 2012, provisional application No. 61/659,029, filed on Jun. 13, 2012, provisional application No. 61/612,008, filed on Mar. 16, 2012, provisional application No. 61/612,005, filed on Mar. 16, 2012, provisional application No. 61/612,087, filed on Mar. 16, 2012.

(51) Int. Cl.
  *G03F 7/20* (2006.01)
  *C12Q 1/686* (2018.01)
  *B01L 7/00* (2006.01)

(52) U.S. Cl.
  CPC .......... *C12Q 1/6806* (2013.01); *C12Q 1/686* (2013.01); *G03F 7/2002* (2013.01); *B01L 7/52* (2013.01); *B01L 2200/0642* (2013.01); *B01L 2200/142* (2013.01); *B01L 2300/046* (2013.01); *B01L 2300/0654* (2013.01); *B01L 2300/0829* (2013.01); *B01L 2300/0893* (2013.01); *B01L 2300/0896* (2013.01); *B01L 2300/161* (2013.01)

(58) Field of Classification Search
  CPC .............. B01L 3/5025; B01L 3/50857; B01L 2200/0642; B01L 2200/0605; B01L 3/5027; B01L 2400/0406; B01L 3/0248; G01N 2035/1037; G01N 35/10
  See application file for complete search history.

(56) References Cited

U.S. PATENT DOCUMENTS

| | | | |
|---|---|---|---|
| 2003/0194353 A1* | 10/2003 | Gilbert | B01L 3/0248 422/520 |
| 2004/0022681 A1* | 2/2004 | Hantschel | B41J 2/14314 506/8 |
| 2004/0132166 A1 | 7/2004 | Miller et al. | |
| 2004/0208792 A1 | 10/2004 | Linton et al. | |
| 2005/0112634 A1 | 5/2005 | Woudenberg et al. | |
| 2005/0221358 A1* | 10/2005 | Carrillo | B01L 3/50853 435/6.16 |
| 2006/0019333 A1 | 1/2006 | Rodgers et al. | |
| 2006/0088857 A1* | 4/2006 | Attiya | C12Q 1/6869 435/6.12 |
| 2006/0263263 A1* | 11/2006 | Shimizu | G01N 21/05 422/68.1 |
| 2006/0281183 A1 | 12/2006 | Sun et al. | |
| 2007/0099208 A1 | 5/2007 | Drmanac et al. | |
| 2007/0178023 A1 | 8/2007 | Russo et al. | |
| 2009/0062152 A1 | 3/2009 | Linton et al. | |
| 2009/0225410 A1 | 9/2009 | Fey | |
| 2011/0207137 A1 | 8/2011 | Malik et al. | |

FOREIGN PATENT DOCUMENTS

| | | |
|---|---|---|
| WO | WO-03018772 A2 | 3/2003 |
| WO | WO-2005028629 A2 | 3/2005 |

OTHER PUBLICATIONS

Heyries, et al., "Megapixel Digital PCR", Nature Methods, vol. 8, No. 8, 2011, Pas 649-651.

International Preliminary Report on Patentability for Application No. PCT/US2013/032420 dated Sep. 16, 2014.

International Search Report and Written Opinion for Appl. No. PCT/US2013/032420 dated Jul. 26, 2013.

Margulies et al., "Genome Sequencing in Microfabricated High-Density Picolitre Reactors", Nature, vol. 437, No. 15, 2005, pp. 376-380.

* cited by examiner

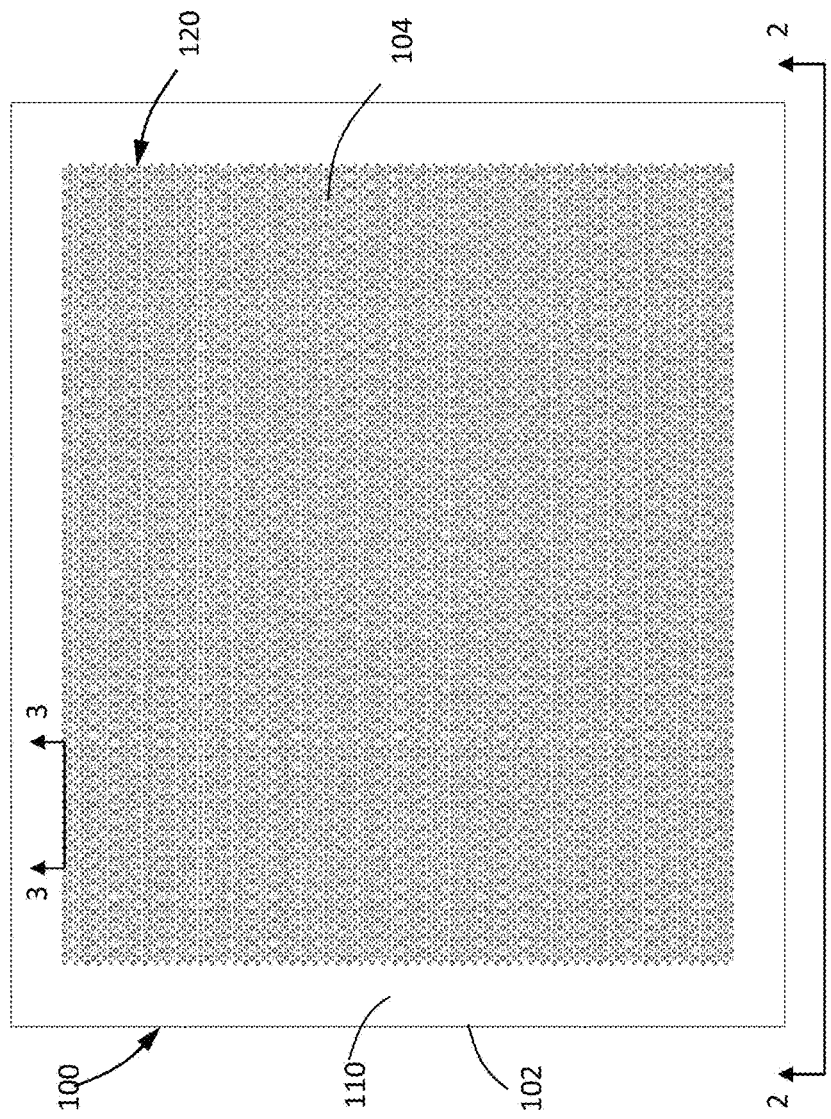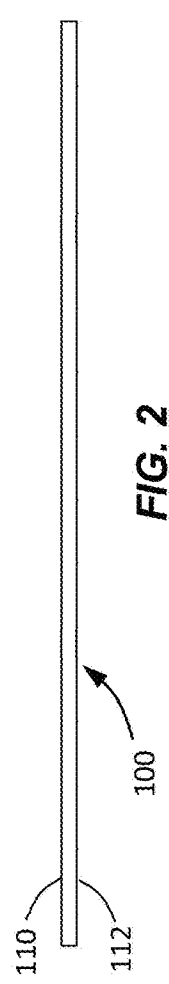

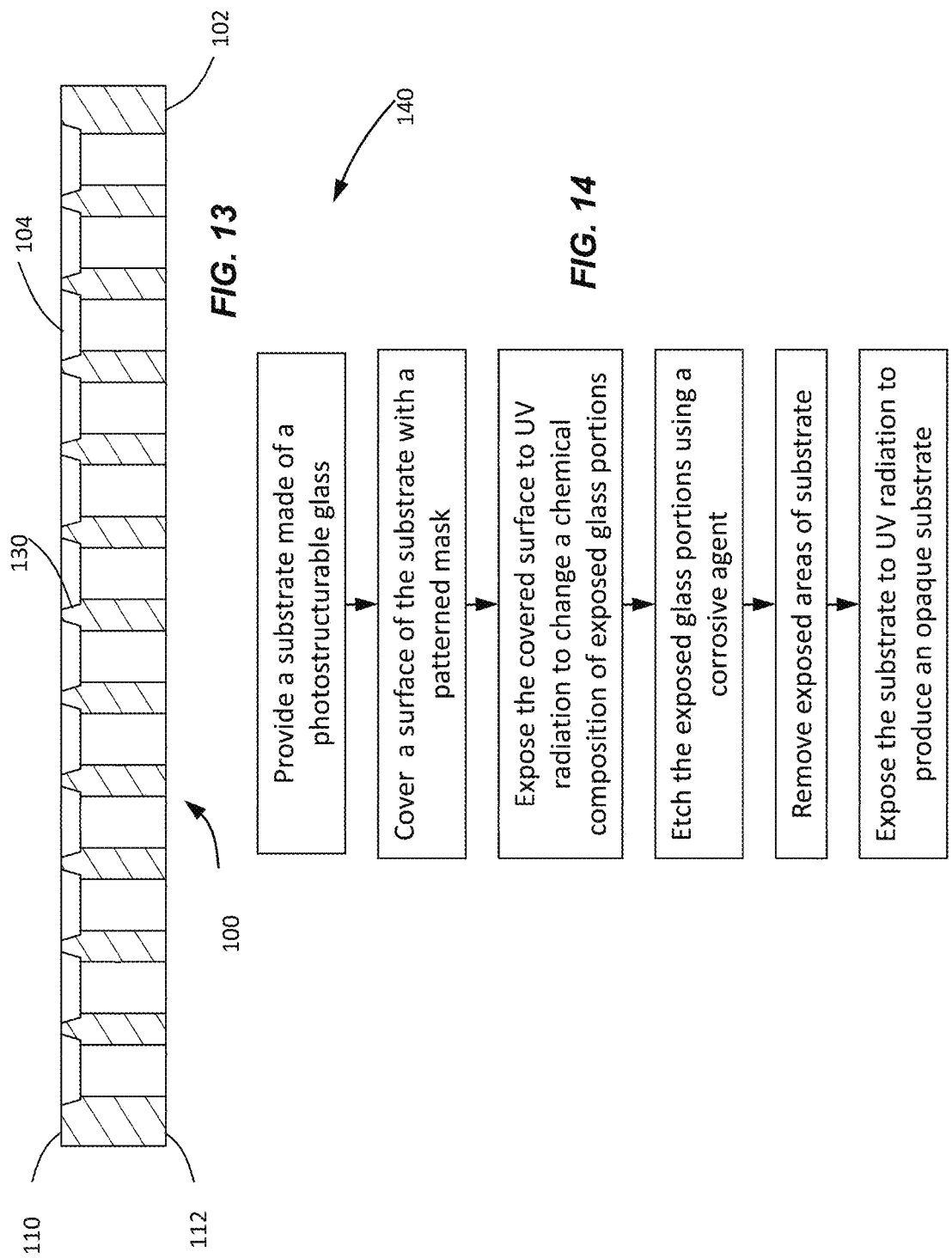

SYSTEMS AND METHODS FOR BIOLOGICAL ANALYSIS

CROSS-REFERENCE TO RELATED APPLICATIONS

This application is a divisional of U.S. patent application Ser. No. 14/385,730 filed Sep. 16, 2014, which claims the benefit of priority of U.S. Provisional Patent Application No. 61/612,005 filed on Mar. 16, 2012, U.S. Provisional Patent Application No. 61/612,087 filed on Mar. 16, 2012, U.S. Provisional Patent Application No. 61/723,759 filed on Nov. 7, 2012, U.S. Provisional Patent Application No. 61/612,008 filed Mar. 16, 2012, U.S. Provisional Patent Application No. 61/723,658 filed Nov. 7, 2012, U.S. Provisional Patent Application No. 61/723,738 filed on Nov. 7, 2012, U.S. Provisional Patent Application No. 61/659,029 filed Jun. 13, 2012, U.S. Provisional Patent Application No. 61/723,710 filed Nov. 7, 2012, and U.S. Provisional Application No. 61/774,499 filed Mar. 7, 2013, all of which are also incorporated herein in their entirety by reference.

BACKGROUND

Systems for biological and biochemical reactions have been used to monitor, measure, and/or analyze such reactions in real time. Such systems are commonly used in sequencing, genotyping, polymerase chain reaction (PCR), and other biochemical reactions to monitor the progress and provide quantitative data.

Polymerase Chain Reaction (PCR) is a method of amplifying a target DNA sequence. Previously, PCR has been generally performed in 96- or 384-well microplates. If higher throughputs are desired, conventional PCR methods in microplates are not cost effective or efficient. On the other hand, reducing the PCR reaction volumes lowers the consumption of reagents and may decrease amplification times from the reduced thermal mass of the reaction volumes. This strategy may be implemented in an array format (m×n), resulting in a large number of smaller reaction volumes. Furthermore, using an array allows for a scalable high throughput analysis with increased quantification sensitivity, dynamic range, and specificity.

Array formats have also been used to perform Digital Polymerase Chain Reaction (dPCR). Results from dPCR can be used to detect and quantify the concentration of rare alleles, to provide absolute quantitation of nucleic acid samples, and to measure low fold-changes in nucleic acid concentration. Generally, increasing the number of replicates increases the accuracy and reproducibility of dPCR results.

The array format in most quantitative polymerase chain reaction (qPCR) platforms is designed for sample-by-assay experiments, in which PCR results need to be addressable for post-run analysis. For dPCR, however, the specific position or well of each PCR result may be immaterial and only the number of positive and negative replicates per sample may be analyzed.

In dPCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the sample containing the target nucleotide sequence are amplified and produce a positive detection signal, while the samples containing no target nucleotide sequence are not amplified and produce no detection signal.

Thus, increasing demands to provide greater numbers of reactions per test or experiment have resulted in instruments that are able to conduct ever higher numbers of reactions simultaneously.

The increase in the number sample sites in a test or experiment has led to microtiter plates and other sample formats that provide ever smaller sample volumes. In addition, techniques such as digital PCR (dPCR) have increased the demand for smaller sample volumes that contain either zero or one target nucleotide sequence in all or the majority of a large number of test samples. There is a need for systems and sample format that will provide reliable data in a high-density sample format.

SUMMARY

A system for performing biological reactions is provided. The system includes a chip including a substrate and a plurality of reaction sites. The plurality of reaction sites are each configured to include a liquid sample of at most one nanoliter. Further, the system includes a control system configured to initiate biological reactions within the liquid samples. The system further includes a detection system configured to detect biological reactions on the chip. According to various embodiments, the chip includes at least 20000 reaction sites. In other embodiments, the chip includes at least 30000 reaction sites.

DESCRIPTION OF THE FIGURES

FIG. 1 illustrates a chip including a plurality of reaction sites according to various embodiments described herein;

FIG. 2 illustrates a side view of the exemplary chip of FIG. 1 according to various embodiments described herein;

FIG. 13 illustrates a cross-section of a substrate including a plurality of through-holes with an exemplary shape according to various embodiments;

FIG. 14 illustrates an exemplary method of fabricating a chip according to various embodiments described herein;

DETAILED DESCRIPTION

Figure 3:
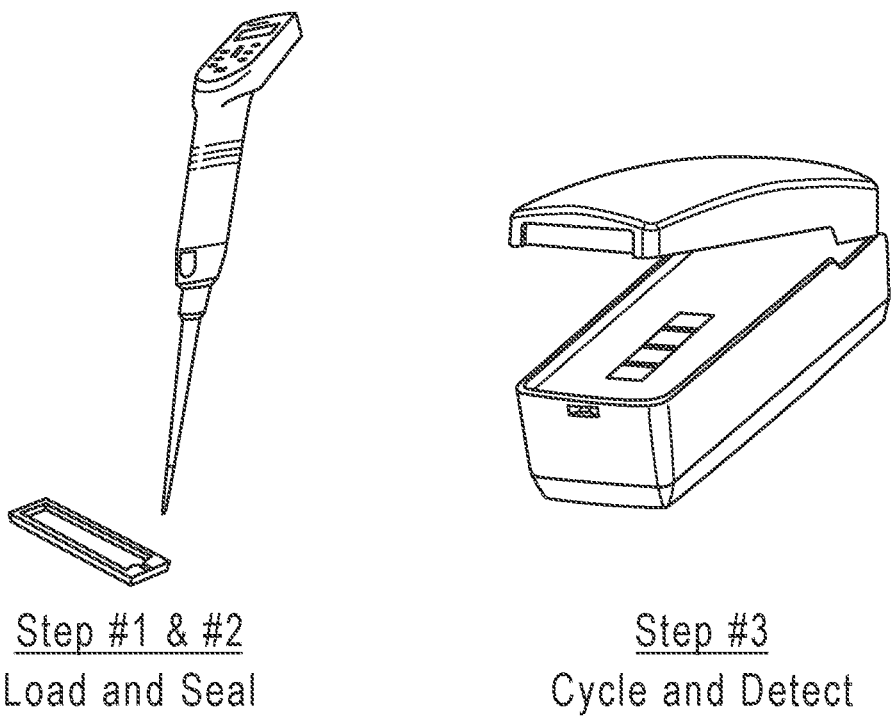
FIG. 3 illustrates an exemplary method of performing biological reactions according to various embodiments described herein.

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

In various embodiments, the devices, instruments, systems, and methods described herein may be used to detect one or more types of biological components or targets of interest that are contained in an initial sample or solution. These biological components or targets may be any suitable biological target including, but not limited to, DNA sequences (including cell-free DNA), RNA sequences, genes, oligonucleotides, molecules, proteins, biomarkers, cells (e.g., circulating tumor cells), or any other suitable target biomolecule. In various embodiments, such biological components may be used in conjunction with one or more PCR methods and systems in applications such as fetal diagnostics, multiplex dPCR, viral detection, quantification standards, genotyping, sequencing assays, experiments, or protocols, sequencing validation, mutation detection, detection of genetically modified organisms, rare allele detection, and/or copy number variation.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. Embodiments of the present disclosure are generally directed to devices, instruments, systems, and methods for monitoring or measuring a biological reaction for a large number of small volume samples. As used herein, samples may be referred to as sample volumes, or reactions volumes, for example.

While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, cast PCR, qPCR, genome walking, and bridge PCR, for example.

As described below, in accordance with various embodiments described herein, reaction sites may include, but are not limited to, through-holes, wells, indentations, spots, cavities, sample retainment regions, and reaction chambers, for example.

Furthermore, as used herein, thermal cycling may include using a thermal cycler, isothermal amplification, thermal convention, infrared mediated thermal cycling, or helicase dependent amplification, for example. In some embodiments, the chip may be integrated with a built-in heating element. In various embodiments, the chip may be integrated with semiconductors.

According to various embodiments, detection of a target may be, but is not limited to, fluorescence detection, detection of positive or negative ions, pH detection, voltage detection, or current detection, alone or in combination, for example.

Various embodiments described herein are particularly suited for digital PCR (dPCR). In digital PCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the sample containing the target nucleotide sequence are amplified and produce a positive detection signal, while the samples containing no target nucleotide sequence are not amplified and produce no detection signal. Using Poisson statistics, the number of target nucleotide sequences in the original solution may be correlated to the number of samples producing a positive detection signal.

In some embodiments, the detected signal may be used to determine a number, or number range, of target molecules contained in an individual sample or volume. For example, a detection system may be configured to distinguish between samples containing one target molecule and samples containing two or at least two target molecules. Additionally or alternatively, the detection system may be configured to distinguish between samples containing a number of target molecules that is at or below a predetermined amount and samples containing more than the predetermined amount. In certain embodiments, both qPCR and dPCR processes, assays, or protocols are conducted using a single device, instrument, or system.

Figure 27:
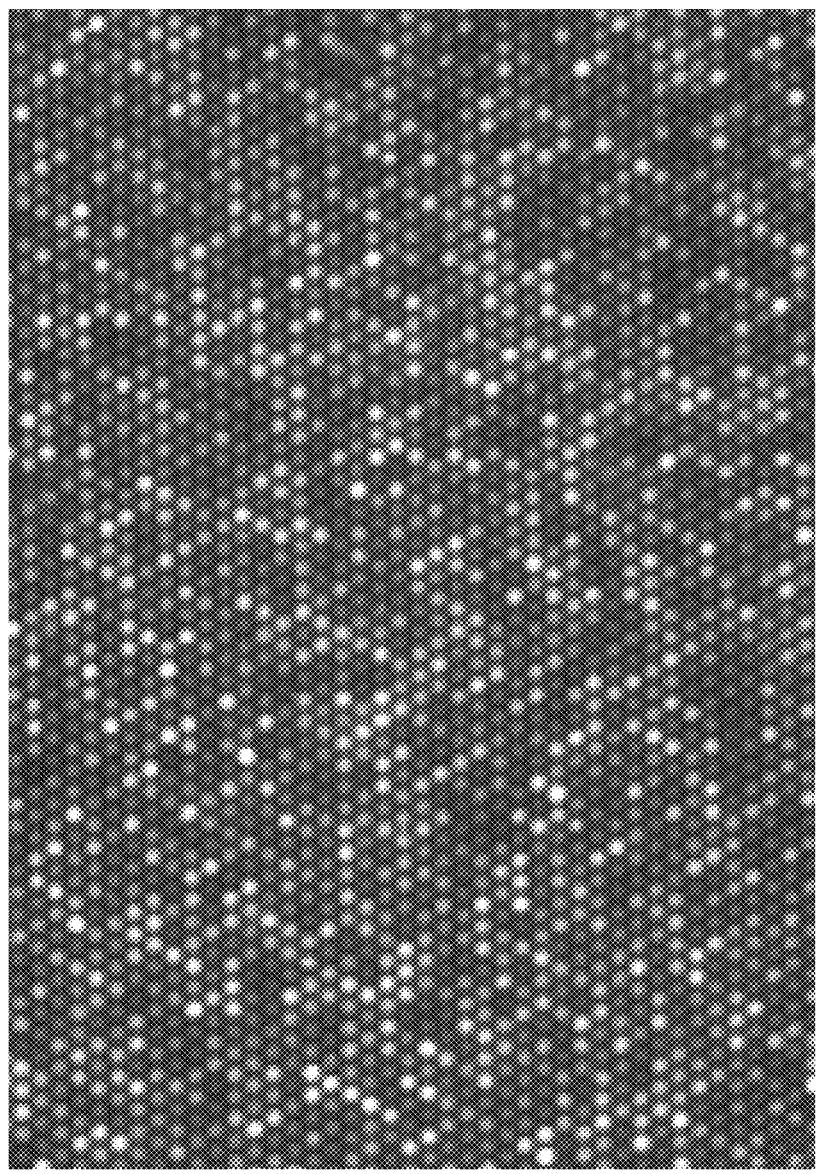
FIG. 27 illustrates a biological reaction result of samples loaded according to various embodiments described herein.

An exemplary dPCR result on a chip according to embodiments described herein is shown in FIG. 27.

In certain embodiments, a dPCR protocol, assay, process, or experiment included distributing or dividing an initial sample or solution into at least ten thousand reaction sites, at least a hundred thousand reaction sites, at least one million reaction sites, or at least ten million of reaction sites. Each reaction site may have a volume of a few nanoliters, about one nanoliter, or that is less than or equal to one nanoliter (e.g., less than or equal to 100 picoliters, less than or equal to 10 picoliters, and/or less than or equal to one picoliter). When the number of target nucleotide sequences contained in the initial sample or solution is very small (e.g., less than 1000 target molecules, less than 100 target, less than 10 target molecules, or only one or two target molecules), it may also be important in certain cases that the entire content, or nearly the entire content, of the initial solution be contained in or received by the sample volumes or reaction sites being processed. For example, where there are only a few target nucleotides present in the initial solution, some or all of these target nucleotide could potentially be contained in a small residual fluid volume that are not located in any of the reaction sites and, therefore, would not be detected, measured, or counted. Thus, efficient transfer of the initial solution may aid in reducing the chances or possibility of a miscalculation in the number count of a rare allele or target nucleotide or of failing to detect the presences at all a rare allele or target nucleotide if none of the target molecules are successfully located into one of the designated reaction sites. Accordingly, embodiments of the present invention may be used to provide a high loading efficiency, where loading efficiency is defined as the volume or mass of an initial sample or solution received within the reaction sites divided by the total volume or mass of the initial sample or solution.

Embodiments described herein solve these and other dPCR design constraints by distributing an initial sample solution into a plurality of reaction sites in a way that accounts for all, or essentially all, of sample solution.

In various embodiments, the devices, instruments, systems, and methods described herein may be used to detect one or more types of biological components of interest. These biological components of interest may include, but are not limited to, DNA sequences, RNA sequences, genes, oligonucleotides, or cells (e.g., circulating tumor cells). In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation.

Figure 8:
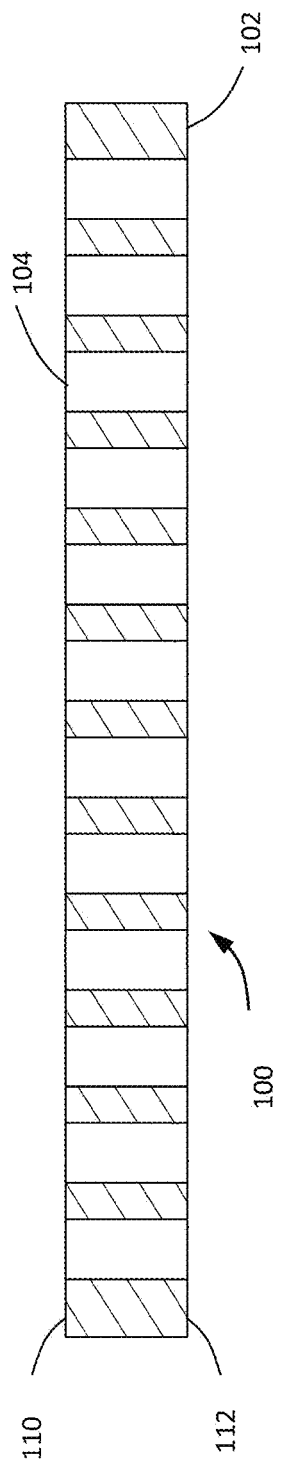
FIG. 8 illustrates a cross-sectional view of a chip according to various embodiments described herein.

Referring to FIGS. 1-2, and 8, in certain embodiments of the present invention, an article, chip, device, substrate, slide, or plate 100 comprises a substrate 102 containing a plurality of through-holes, reaction regions, or reaction sites 104 located in substrate 102. In certain embodiments, chip 100 may comprise an article. Additionally or alternatively, chip 100 may comprise a microfluidic device which, for example, may further include a plurality of channels or paths for transferring reagents and/or test solutions to reaction sites 104. In other embodiments, reaction sites 104 comprise a plurality of droplets or beads and chip 100 may comprise one or more chambers and/or channels containing some or all of the droplets or beads 104. In such embodiments, droplets or beads 104 may form an emulsion, where some or all of droplets or beads 104 contain one or more target of at least one polynucleotide or nucleotide sequence. Where reaction sites 104 are beads, the beams may optionally include an attached optical signature or label. Droplets or beams 104 may be inspected, monitored, or measured either one at time or in groups containing one or more droplets or beads 104, for example using an imaging system according to embodiments of the present invention.

In the illustrated embodiment, chip 100 comprises a first surface 110 and an opposing second surface 112. In the illustrated embodiment, each reaction site 104 extends from an opening 114 in first surface 110 to an opening 116 in second surface 112. While the illustrated embodiment shown in FIG. 8 shows a substrate containing through-holes 104, substrate 102 may additionally or alternatively comprise other types of reaction sites. For example, reaction sites 104 may include reaction volumes located within wells or indentations formed in substrate 102, spots of solution distributed on the surfaces 110 or 112, or other types of reaction chambers or formats, such as samples or solutions located within test sites or volumes of a microfluidic system, or within or on small beads or spheres.

Reaction sites 104 may be configured to provide sufficient surface tension by capillary action to draw in respective amounts of liquid or sample containing a biological components of interest. Chip 100 may have a general form or construction as disclosed in any of U.S. Pat. Nos. 6,306,578; 7,332,271; 7,604,983; 7,6825,65; 6,387,331; or 6,893,877, which are herein incorporated by reference in their entirety as if fully set forth herein. Substrate 102 may be a flat plate or comprise any form suitable for a particular application, assay, or experiment. Substrate 102 may comprise any of the various materials known in the fabrication arts including, but not limited to, a metal, glass, ceramic, silicon, or the like. Additionally or alternatively, substrate 102 may comprise a polymer material such as an acrylic, styrene, polyethylene, polycarbonate, and polypropylene material. Substrate 102 and reaction sites 104 may be formed by one or more of machining, injection molding, hot embossing, laser drilling, photolithography, or the like.

In certain embodiments, surfaces 110, 112 may comprise a hydrophobic material, for example, as described in US Patent Application Publication Numbers 2006/0057209 or 2006/0105453, which are herein incorporated by reference in their entirety as if fully set forth herein. In such embodiments, reaction sites 104 may comprise a hydrophilic material that attracts water or other liquid solutions. An array of such hydrophilic regions may comprise hydrophilic islands on a hydrophobic surface and may be formed on or within substrate 102 using any of various micro-fabrication techniques including, but are not limited to, depositions, plasmas, masking methods, transfer printing, screen printing, spotting, or the like.

It has been discovered that a high reaction site density may be configured to reduce the amount of a solution that is left on surface 110, 112 during a loading process, thus leading to higher loading efficiency or transfer of the initial solution. For example, by reducing ratio of the value of the spacing between adjacent well to the value of the well diameter, the amount of solution left on the surface of a plate may be significantly reduced so that, all, or nearly all, of an initial solution or sample containing biological components of interest is located inside reaction sites 104. In this way the possibility is reduced of missing a rare allele or other target molecule, since it would be less likely that one or more target molecule would remain on the substrate surface instead of being received in one of the designated reaction sites 104.

Figure 7:
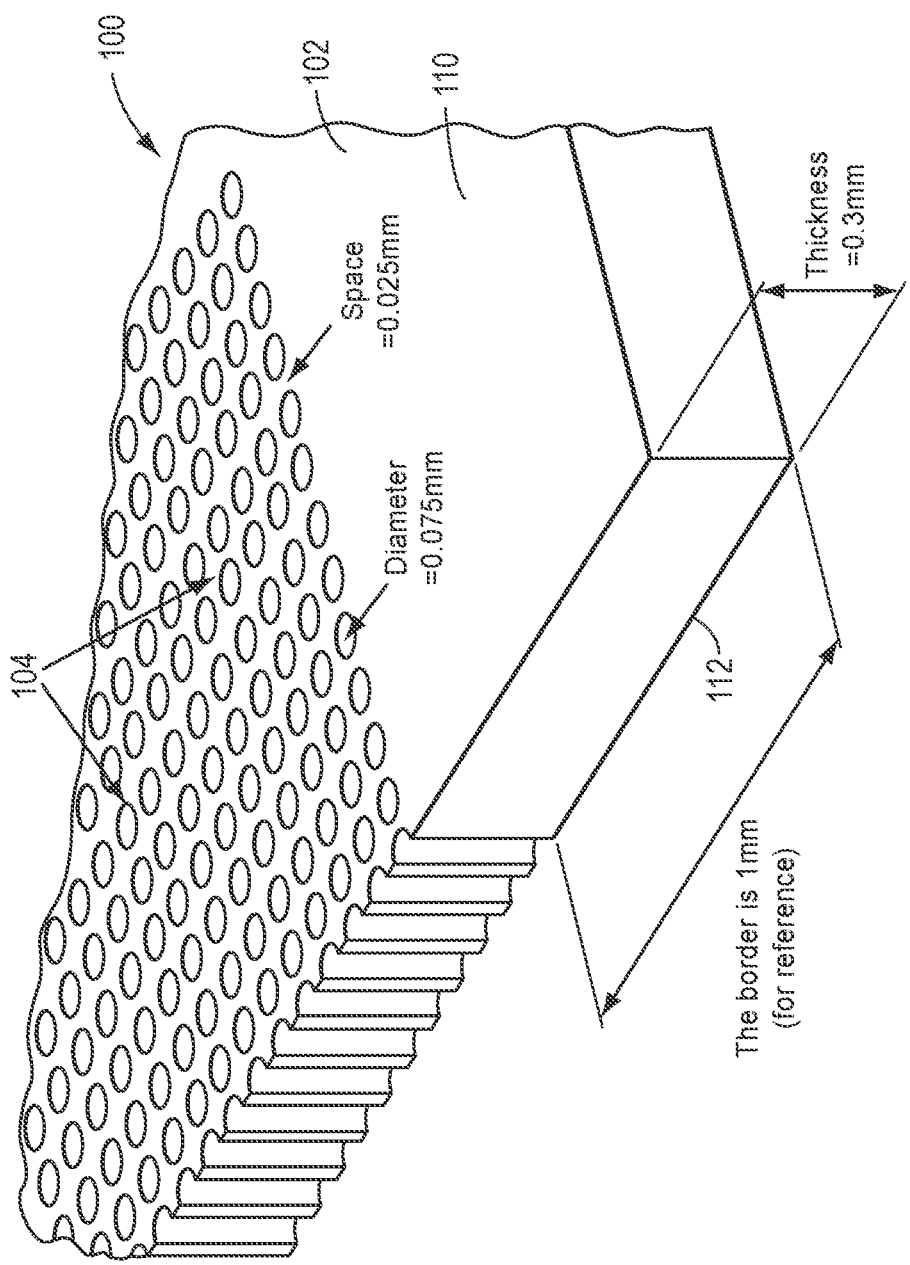
FIG. 7 illustrates a cut away view of an array in a substrate according to various embodiments described herein.

In FIG. 7, each reaction site 104 extends from an opening 114 in first surface 110 to an opening 116 in second surface 112. Reaction sites 104, illustrated in this example of FIG. 7, are through-holes. The reactions sites 104 are configured to provide sufficient surface tension by capillary action to hold respective liquid samples containing a biological sample to be processed or examined. Chip 100 may have a general form or construction as disclosed in any of U.S. Pat. Nos. 6,306,578; 7,332,271; 7,604,983; 7,682,565; 6,387,331; or 6,893,877, which are herein incorporated by reference in their entirety as if fully set forth herein.

Substrate 102 may be a flat plate or comprise any form suitable for a particular application or design. Substrate may comprise, in total or in part, any of the various materials known in the fabrication arts including, but not limited to, a metal, glass, ceramic, silicon material, or the like. Additionally or alternatively, substrate 102 may comprise a polymer material such as an acrylic, styrene, polyethylene, polycarbonate, and polypropylene material. Substrate 102 and reaction sites 104 may be formed by one or more of machining, injection molding, hot embossing, laser drilling, photolithography, or the like.

In certain embodiments, surfaces 110, 112 may comprise a hydrophobic material, for example, as described in US Patent Application Publication Numbers 2006/0057209 or 2006/0105453, which are herein incorporated by reference in their entirety as if fully set forth herein. In such embodiments, reaction sites 104 comprise a hydrophilic material that attracts water or other liquid solutions. An array of such hydrophilic regions may comprise hydrophilic islands on a hydrophobic surface and may be formed on substrate 102 using a wide range of micro-fabrication techniques including, but are not limited to, depositions, plasmas, masking methods, transfer printing, screen printing, spotting, or the like. A coating method for coating embodiments of chip 100 is also described in U.S. provisional application No. 61/723,738, filed on Nov. 7, 2012, which is incorporated herein for all purposes.

Figure 4:
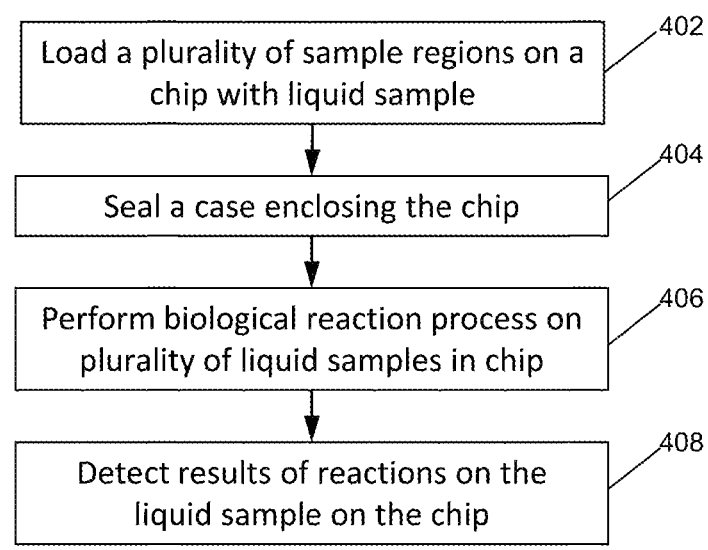
FIG. 4 illustrates an exemplary method of performing biological reactions according to various embodiments described herein.

FIG. 3 depicts an illustration of a workflow of using a system according to various embodiments of the present disclosure. FIG. 4 illustrates a flowchart of an exemplary workflow according to various embodiments. According to various embodiments described herein, the workflow to perform biological reactions on the system is simple and does not require a substantial amount of user performed steps. With reference to FIGS. 1 and 4, in step 402, the array 120 of a plurality of reaction sites 104 is loaded with liquid samples. In some embodiments, a user uses a sample loader to load reaction sites 104. Loading by a sample loader is described in more detail below. In some embodiments, a case for the chip may aid in loading of the liquid samples. Loading of the samples, according to the present teachings, is described in more detail below. Next, in step 404, the case is sealed with the chip inside. The chip may be loaded into an instrument that will perform a biological reaction process, in step 406. The results of the biological reactions are then detected, in step 408, by an optical system, such as the optical system shown in FIG. 6. As mentioned above, for dPCR applications, it is determined how many negative versus positive reactions are present within array 120 to determine a quantity.

Figure 5:
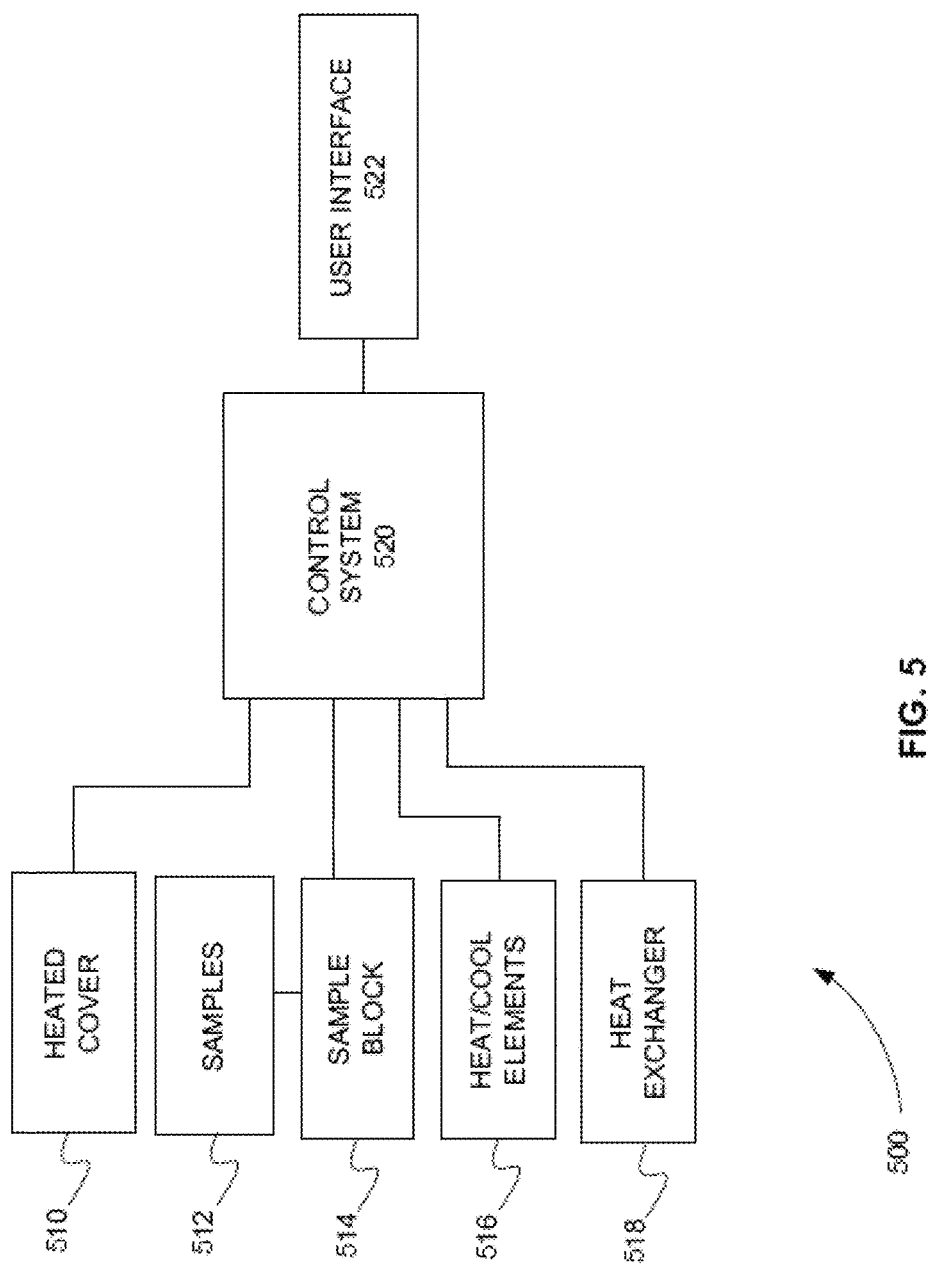
FIG. 5 is a block diagram that illustrates a polymerase chain reaction (PCR) instrument, upon which embodiments of the present teachings may be implemented.

As mentioned above, an instrument that may be utilized according to various embodiments, but is not limited to, is a polymerase chain reaction (PCR) instrument. FIG. 5 is a block diagram that illustrates a PCR instrument 500, upon which embodiments of the present teachings may be implemented. PCR instrument 500 may include a heated cover 510 that is placed over a plurality of samples 512 contained in a sample support device (not shown). In various embodiments, a sample support device may be a chip, or glass or plastic slide with a plurality of reaction sites, which reaction sites have a cover between the reaction sites and heated cover 510. Some examples of a sample support device may include, but are not limited to, a chip according to embodiments of the present teachings, a multi-well plate, such as a standard microtiter 96-well, a 384-well plate, or a microcard, or a substantially planar support, such as a glass or plastic slide. The reaction sites in various embodiments may include depressions, indentations, ridges, and combinations thereof, patterned in regular or irregular arrays formed on the surface of the substrate.

Various embodiments of PCR instruments include a sample block 514, elements for heating and cooling 516, a heat exchanger 518, control system 520, and user interface 522. Various embodiments of a thermal block assembly according to the present teachings comprise components 514-518 of PCR instrument 500 of FIG. 5.

According to other embodiments of the present teachings, the thermal block assembly includes thermal electric devices such that substantial uniform heat transfer is provided throughout the thermal block assembly. Embodiments of this configuration are described further in U.S. patent application Ser. No. 12/874,112 which is incorporated herein by reference in its entirety as if fully set forth herein.

In instruments configured for a certain sample support, an adaptor may be provided, so that PCR instrument 1000 may use chip 100 according to various embodiments. The adapter is configured to allow efficient heat transfer to the samples within chip 100.

In other embodiments, the chip may include integrated heating elements.

Figure 26:
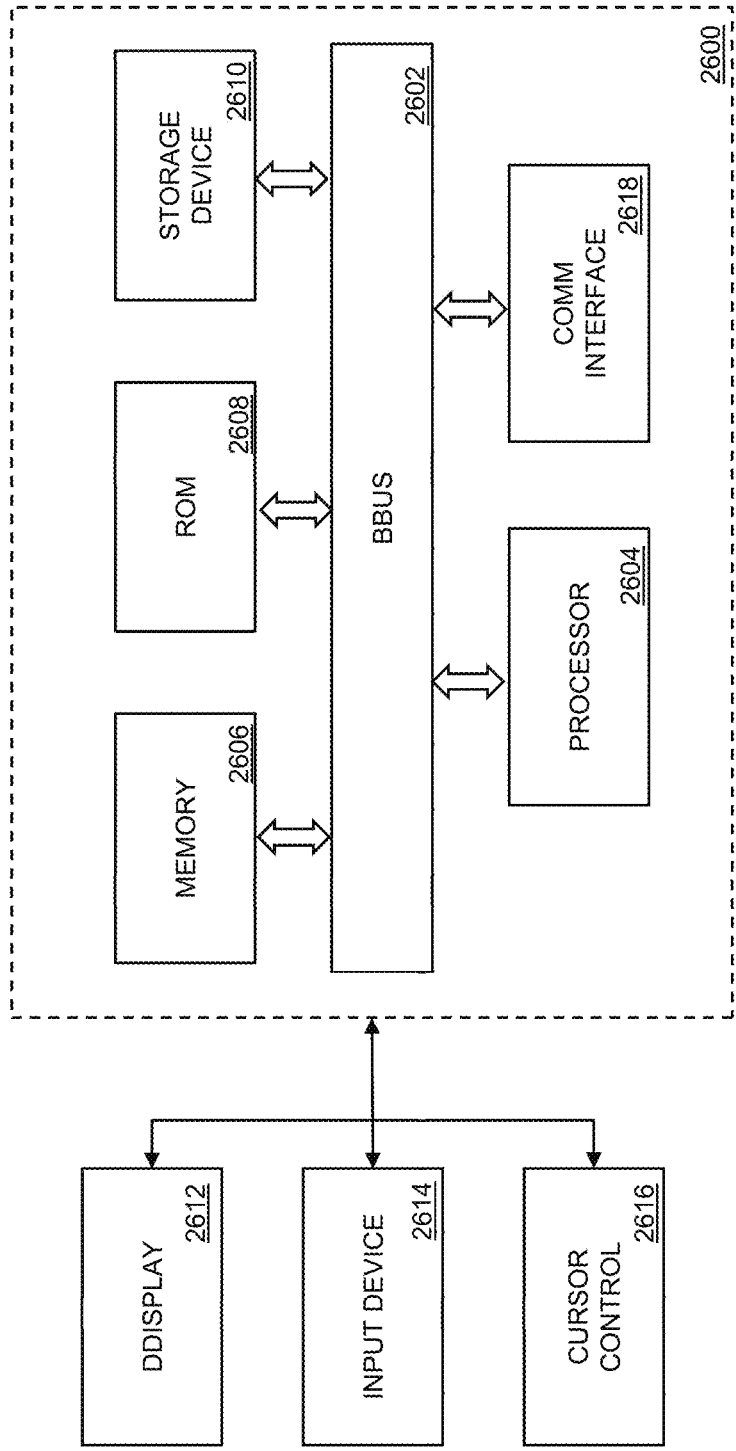
FIG. 26 is a block diagram that illustrates a computer system, upon which embodiments of the present teachings may be implemented.

For embodiments of PCR instrument 500 in FIG. 5, control system 520, may be used to control the functions of the detection system, heated cover, and thermal block assembly. Control system 520 may be accessible to an end user through user interface 522 of PCR instrument 500 in FIG. 5. Also a computing system 2600, as depicted in FIG. 26, may serve as to provide the control the function of PCR instrument 500 in FIG. 5, as well as the user interface function. Additionally, computing system 300 of FIG. 26 may provide data processing, display and report preparation functions. All such instrument control functions may be dedicated locally to the PCR instrument, or computer system 2600 of FIG. 26 may provide remote control of part or all of the control, analysis, and reporting functions, as will be discussed in more detail subsequently. Instrument control functions may be provided on the instrument, accessible through a graphical user interface (GUI). Further, in various embodiments, data analysis controls may be provided on the instrument, accessible through a GUI. In various embodiments, data analysis of the results of the system may be performed at a local computer system, connected to the instrument. In other embodiments, data analysis functions may be accessed over a network by a user. Data from performing biological reactions by the system, according to various embodiments, may be stored on a server system to be accessible by users over a network.

As mentioned above, detection of the target may include fluorescence detection, detection of positive or negative ions, pH detection, voltage detection, or current detection, for example. As such, a detection system, according to various embodiments described herein may include an optical system, an electrical detection system, an ion detection system, or a pH detection system, for example. According to various embodiments, the detection system may be integrated in the chip.

Figure 6:
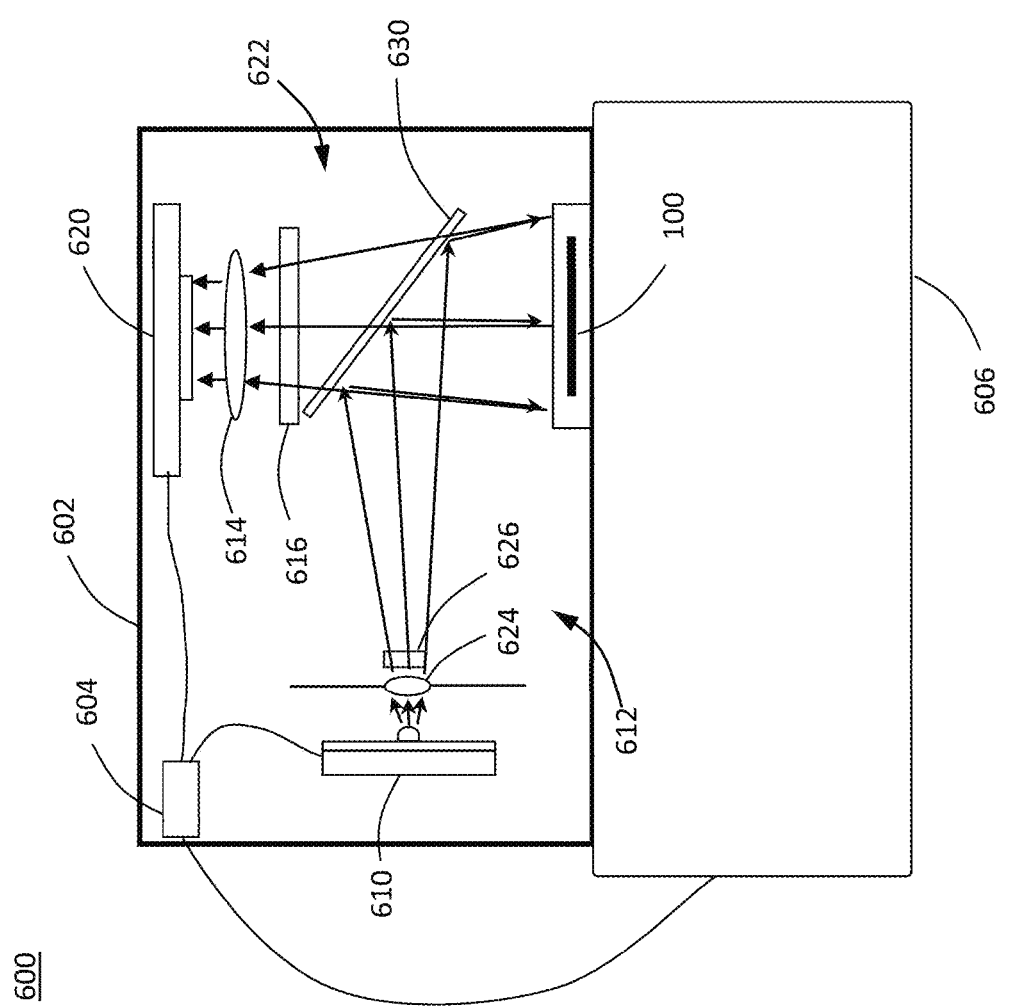
FIG. 6 illustrates an exemplary optics system that can be used to image the chip according to embodiments of the present teachings.
Figure 23:
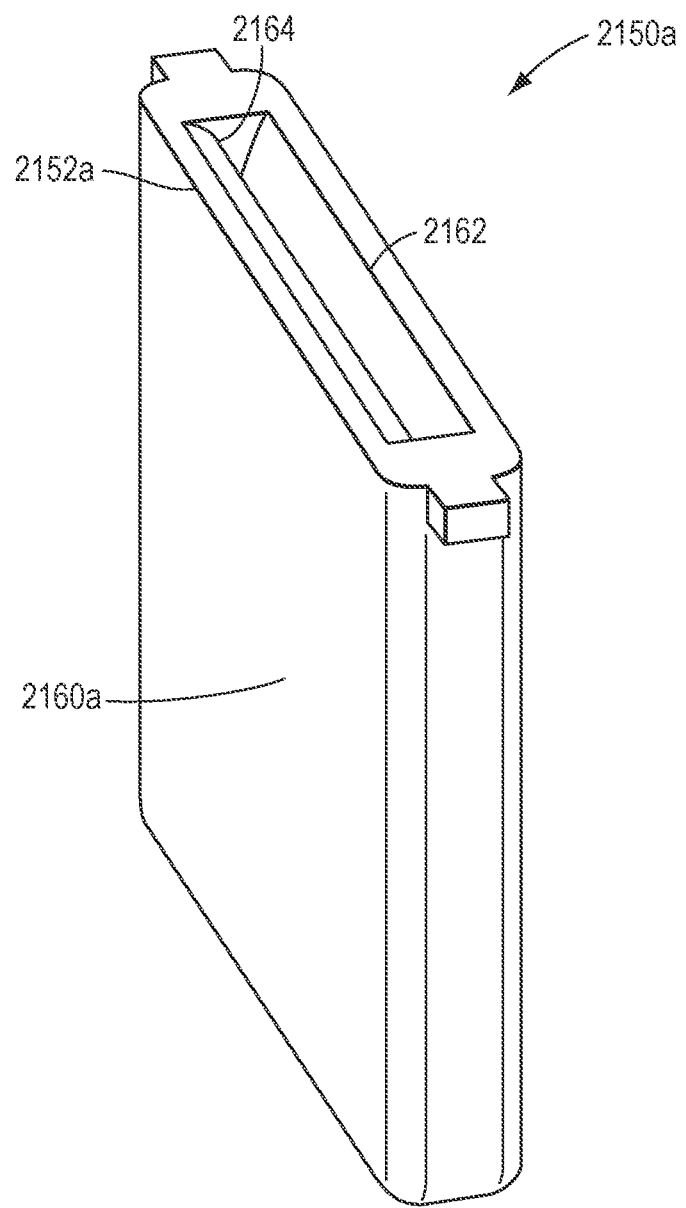
FIG. 23 illustrates a perspective view of a carrier according to embodiments of the present teachings.

Referring to FIG. 6, as mentioned above, a system 600 may be used optically view, inspect, detect, or measure one or more targets contained in the reaction sites of chip 100, which may be contained in a carrier such as carrier 2150a with reference to FIG. 23. System 600 comprises an optical head or system 602. System 600 may further comprise a controller, computer, or processor 604 configured, for example, to operate various components of optical system 602 or to obtain and/or process data provided by system 600. For example, processor 604 may be used to obtain and/or process optical data provided by one or more photodetectors of optical system 602. In other embodiments, processor 604 may transmit data to one or more computing systems for further processing. Data may be transmitted from processor 604 to the computing systems, via a network, in some embodiments.

In certain embodiments, system 600 further comprises a thermal control system 606 comprising, for example, a thermal cycler configured to perform a PCR procedure or protocol on at least some of the samples contained in chip 100. Systems 602, 606 may combined or coupled together into a single unit, for example, in order to perform a qPCR and/or a dPCR procedure or protocol on at least some of the samples contained in chip 100. In such embodiments, computer 604 may be used to control systems 602, 606 and/or to collect or process data provided or obtained by either or both systems 602, 606. In other embodiments, system 602 and system 606 may be independent units.

In certain embodiments, optical system 602 comprises a light source 610 and an associated excitation optic system 612 configured to illuminate at least some of samples contained in the reaction sites of chip 100. Excitation optical system 612 may include one or more lenses 614 and/or one or more filters 616 for conditioning light directed to the samples. Optical system 602 may further comprise a photodetector 620 and an associated emission optic system 622 configured to receive optical data emitted by at least some of samples contained in the reaction sites of chip 100. For example, when system 600 is configured to perform a qPCR and/or a dPCR procedure, the sample may contain fluorescent dyes that provide a fluorescent signal that varies according to an amount of target nucleotide sequence contained in various of the through-holes of chip 100. Emission optical system 622 may include one or more lenses 624 and/or one or more filters 626 for conditioning light directed to the samples.

According to various embodiments, optical system 602 may have a focal length of 15 mm and a working distance of 60 mm, where the working distance of the distance from the chip to the camera lens. Furthermore, in various embodiments, the overall system F-number is less than or equal to 3.

In the illustrated embodiment of FIG. 6, excitation/emission optical systems 612, 622 both comprise one or more common optical elements. For example, excitation/emission optical systems 612, 622 both comprise a beamsplitter 630 that reflects excitation light and transmits emission light from the samples to photodetector 620. In certain embodiments, excitation/emission optical systems 612, 622 both comprise a field lens (not shown) disposed between beamsplitter 630 and chip 100, which may be used improve optical performance, for example, to provide more even illumination and reading of light to and from the samples contained in chip 100. In certain embodiments, for example where even illumination is less critical (e.g., some dPCR applications), the common field lens may be omitted, as shown in the illustrated embodiment of FIG. 6. Omission of the field lens may help to reduce the size and complexity of optical system 602.

Advantageously, with reference to FIG. 1, all of the reaction sites 104 in active area 120 may be simultaneously imaged and analyzed by an optical system, as illustrated in FIG. 6. In the illustrated embodiment of FIG. 1, active area 120 comprises over 12,000 reaction sites 104. In other embodiments, active area 120 comprises at least 25,000 reaction sites 104, at least 30,000 reaction sites 104, at least 100,000 reaction sites 104, or at least 1,000,000 reaction sites 104.

FIG. 7 shows an illustrated cross-sectional view of an array of through-holes 104 according to various embodiments. FIG. 8 illustrates another cross-sectional view of chip 100. Chip 100 has a first surface 110 and a second surface 112. Each reaction site 104 extends from an opening in first surface 110 to an opening in second surface 112. Reaction sites 104 are configured to provide sufficient surface tension by capillary action to hold respective liquid samples containing a biological sample to be processed or examined. In the example of FIG. 8, the reaction sites are through-holes.

In the illustrated embodiment, chip 100 has a thickness between first surface 110 and second surface 112 of 300 micrometers, so that each reaction site 104 has a volume of about 1.3 nanoliters. Alternatively, the volume each reaction site may be less than 1.3 nanoliters. This may be achieved, for example, by decreasing the diameter of reaction site 104 and/or the thickness of substrate 102. For example, each reaction site 104 may have a volume that is less than or equal to 1 nanoliter, less than or equal to 100 picoliters, less than or equal to 30 picoliters, or less than or equal to 10 picoliters. In other embodiments, the volume some or all of the reaction sites 104 is in a range of 1 to 20 nanoliters.

In some embodiments, the reaction sites are through-holes. In these examples, each through-hole has a volume of about 1.3 nanoliters. Alternatively, the volume each through-hole may be less than 1.3 nanoliters. This may be achieved, for example, by decreasing the diameter of through-hole and/or the thickness of substrate 102. For example, each through-hole may have a volume that is less than or equal to 1 nanoliter, less than or equal to 100 picoliters, less than or equal to 30 picoliters, or less than or equal to 10 picoliters. In other embodiments, the volume some or all of the through-holes is in a range of 1 to 20 nanoliters.

In various embodiments, a density of reaction sites 104 may be at least 100 reaction sites per square millimeter. In other embodiments, there may be higher densities of reaction sites. For example, a density of reaction sites 104 within chip 100 may be greater than or equal to 150 reaction sites per square millimeter, greater than or equal to 200 reaction sites per square millimeter, greater than or equal to 500 reaction sites per square millimeter, greater than or equal to 1,000 reaction sites per square millimeter, greater than or equal to 10,000 reaction sites per square millimeter.

In some embodiments, the reaction sites are through-holes. Accordingly, a density of through-holes within chip 100 may be greater than or equal to 150 through-holes per square millimeter, greater than or equal to 200 through-holes per square millimeter, greater than or equal to 500 through-holes per square millimeter, greater than or equal to 1,000 through-holes per square millimeter, greater than or equal to 10,000 through-holes per square millimeter.

Other embodiments of chip 100 are further described in provisional applications 61/612,087, filed on Mar. 16, 2012, and 61/723,759, filed Nov. 7, 2012, which are incorporated herein for all purposes.

In certain embodiments, an increased reaction site density increases the total number of reaction sites per unit area and, advantageously, the total number of samples that may be contained in a substrate of given dimensions. In addition, chip 100 may be configured to reduce the amount of a solution that is left on surface 110, 112 during a loading procedure so that all, or nearly all, of the solution is contained inside reaction sites 104.

Figure 9:
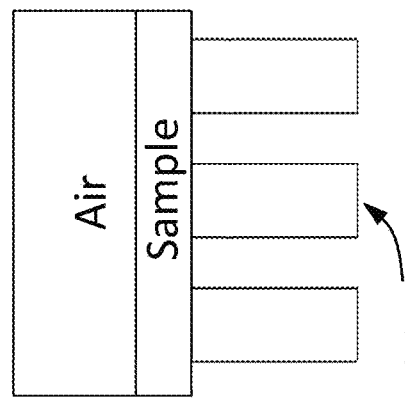
FIG. 9 illustrates a hydrophobic surface and through-holes according to various embodiments described herein.
Figure 10:
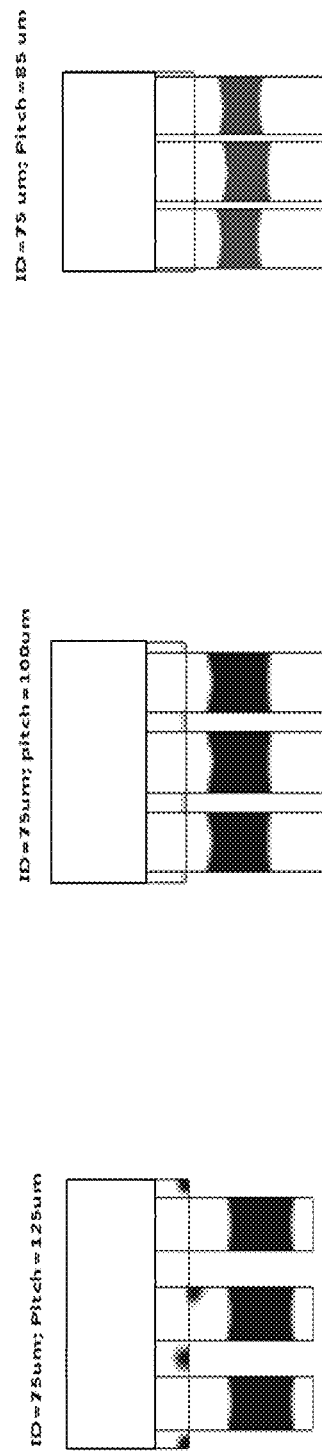
FIG. 10 illustrates various pitch distances according to various embodiments described herein.

Referring to FIG. 9, an increase in loading efficiency was demonstrated with a computer model of a hydrophobic surface containing a plurality of hydrophilic reaction sites. The model was used to analyze the distribution of a sample into the plurality of reaction sites as a function of the reaction site pitch (or density) for through-holes having a diameter of 75 micrometers. FIG. 10 demonstrates that as the spacing between reaction sites is decreased (increased density), a greater percentage of an initial liquid sample is captured by the reaction sites, and a lesser amount of residual liquid is left behind on the hydrophobic surface after the loading process. Thus, a higher density of reaction sites 104 of a given cross-sectional dimension provides both an increase in the number of test samples for a given size substrate 102 and decreases or eliminates residual fluid left on surfaces 110, 112 (which may contain a rare allele or other target molecule of interest).

A sample of the results are shown in FIG. 10, demonstrating that as the spacing between reaction sites is decreased, a greater percentage of a liquid sample is captured by the through-holes and a lesser amount of residual liquid is left on the hydrophobic surface after the modeled loading process. Thus, a higher density of reaction sites 104 of a given cross-sectional dimension generally provides both an increase in the number of samples that may be processed in a given size substrate 102 and a reduction of undesirable residual fluid being left on surfaces 110, 112.

Figure 11:
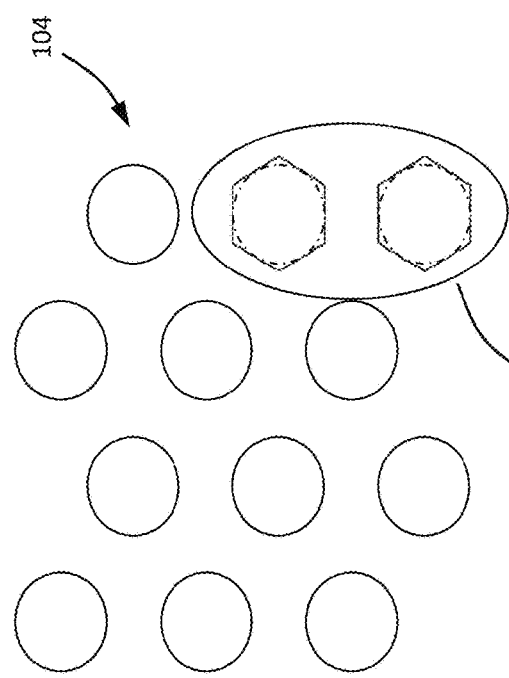
FIG. 11 illustrates an exemplary array of through-holes according to embodiments described herein.
Figure 12:
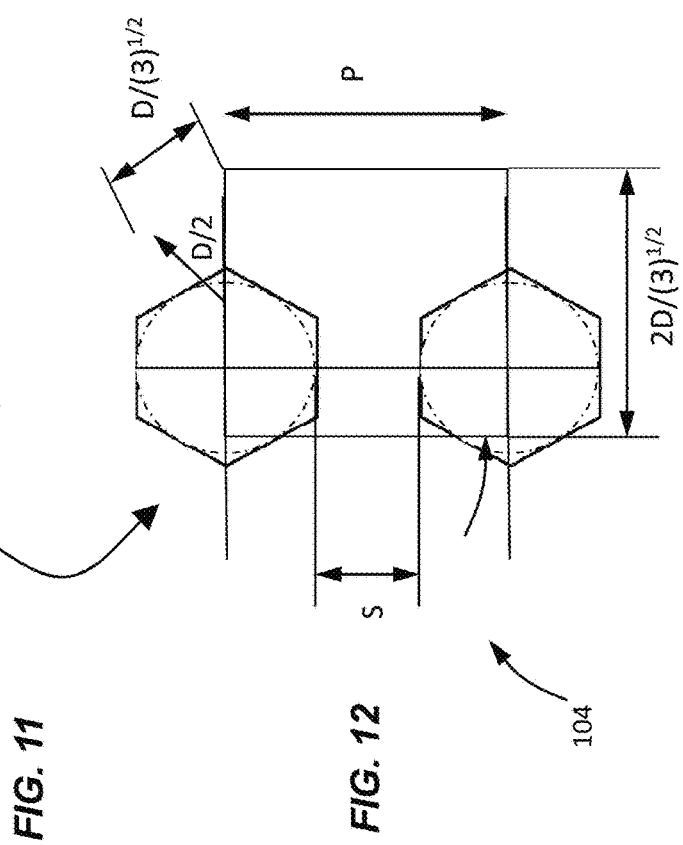
FIG. 12 illustrates a hexagonal shape of a through-hole according to various embodiments described herein.

In certain embodiments, a lower bound in the spacing between adjacent reaction sites may exist, for example, due to optical limitations when reaction sites 104 are being imaged by an optical system. For example, the lower bound in spacing between adjacent reaction sites may exist because of limitations in the ability of the optical system to distinctly image adjacent reaction sites. To increase the density of reaction sites 104 in a substrate 102, a close-packed hexagonal matrix pattern may be used, for example, as illustrated in FIGS. 11 and 12.

It has been discovered that reaction sites having a non-circular cross-section may advantageously reduce an average distance or spacing between adjacent reaction sites 104, leading to a reduction in the amount of residual liquid or solution left behind on surfaces 110, 112 after loading of a test solution or sample. Referring to FIGS. 11 and 12, an array of hexagonal reaction sites 104 having a vertex-to-vertex diameter D are arranged in a hexagonal pattern in which the spacing or pitch between adjacent reaction sites is P. In certain embodiments, cross-talk between adjacent reaction sites in an optical system used to measure a fluorescence signal from the reaction sites 104 is a function of a minimum edge distance S between adjacent reaction sites. Thus, the geometry shown in FIG. 12 represents a minimum pitch P between reaction sites that can be used and still maintain the cross-talk between adjacent reaction sites at or below a predetermined value. A dash-lined circle is also shown in FIG. 12 inside each hexagon. This represents a circular reaction site of diameter D' having the same values of pitch P and the same edge spacing S as that of the hexagonal reaction site. The grayed portion in FIG. 12 shows the area between adjacent reaction sites over some width W for both the circular and hexagonal reaction sites. As is clearly seen in FIG. 12, the area between adjacent reaction sites over width W is greater for the circular reaction sites than between the hexagonal reaction sites, when the pitch P and the edge spacing S are the same. A smaller area between adjacent reaction sites lead to higher loading efficiency. Thus, based on the results illustrated in FIG. 12, a higher loading efficiency is provided, under the same spacing conditions (P and S), for a hexagonal shaped reaction site than for a circular reaction site.

This result also provides an unexpected advantage for an optical system configured to inspect the reaction sites. Since the minimum edge spacing S in FIG. 12 is the same for both the circular and hexagonal reaction sites, the cross-talk between adjacent reaction sites would be the same or similar for either type of reaction site. However, the cross-sectional area of the hexagonal reaction sites is greater than that of the circular reaction sites, for the same pitch P and edge spacing S. Thus, the image produced by an optical system would have a greater area for hexagonal reaction sites than for circular reaction sites. Accordingly, the larger image produced by the hexagonal reaction site may potentially span a greater number of pixels. A greater number of pixels per reaction site aids in making a more accurate calculation of the signal produced a reaction site. Thus, in addition to providing a higher loading efficiency, the use of hexagonal reaction sites, as shown in FIGS. 11 and 12, may also produce more accurate measurement or calculation of an optical signal or output produce by each reaction site 104 (e.g., measurement or calculation of a fluorescence signal produced in proportion to an amount of a target or dye molecule).

In the illustrated embodiment shown in FIG. 1, chip 100 has a square shape and an overall dimension of 15 millimeter by 15 millimeter. Chip 100 also has an active area, region, or zone 120 with a dimension of 13 millimeter by 13 millimeter. As used herein, the term "active area", "active region", or "active zone" means a surface area, region, or zone of an chip, such as the chip 100, over which reaction sites or solution volumes are contained or distributed. In certain embodiments, the active area of chip 100 may be increased to 14 millimeter by 14 millimeter or larger, for example on a 15 millimeter by 15 millimeter substrate dimension, in order to increase the total number of reaction sites contained on substrate 102. Chip 100 may have other shapes and dimensions. For example, surfaces 110, 112 may be rectangular, triangular, circular, or some other geometric shape. The overall dimensions of chip 100 and active area 120 may be smaller or larger than that for the illustrated embodiment in FIG. 1, depending on the particular design parameters for a given system, assay, or experiment.

In the illustrated embodiment of FIG. 1, reaction sites 104 may have a characteristic diameter of 75 micrometer and be distributed over active area 120 with a pitch of 125 micrometers between adjacent reaction sites. In other embodiments, reaction sites 104 have a characteristic diameter of that is less than or equal 75 micrometers, for example, a characteristic diameter that is less than or equal to 60 micrometers or less than or equal to 50 micrometers. In other embodiments, reaction sites 104 have a characteristic diameter that is less than or equal to 20 micrometers, less than or equal to 10 micrometers, less than or equal to 1 micrometer, or less than or equal to 100 nanometers. The pitch between reaction sites may be less than 125 micrometers, for example, less than or equal to 100 micrometers, less than or equal to 30 micrometers, less than or equal to 10 micrometers, or less than or equal to 1 micrometer.

In certain embodiments, substrate 102 has a thickness between surface 110 and surface 112 that is equal to or about 300 micrometer, so that each reaction site 104 has a volume of about 1.3 nanoliters. Alternatively, the volume of each reaction site 104 may be less than 1.3 nanoliters, for example, by decreasing the diameter of reaction sites 104 and/or the thickness of substrate 102. For example, each reaction site 104 may have a volume that is less than or equal to 1 nanoliter, less than or equal to 100 picoliters, less than or equal to 30 picoliters, or less than or equal to 10 picoliters. In other embodiments, the volume some or all of the reaction site 104 is in a range from 1 nanoliter to 20 nanoliters.

In certain embodiments, the density of reaction sites 104 over surfaces 110, 112 is at least 100 reaction sites per square millimeter. Higher densities are also anticipated. For example, a density of reaction sites 104 over surfaces 110, 112 may be greater than or equal to 150 reaction sites per square millimeter, greater than or equal to 200 reaction sites per square millimeter, greater than or equal to 500 reaction sites per square millimeter, greater than or equal to 1,000 reaction sites per square millimeter, greater than or equal to 10,000 reaction sites per square millimeter, or greater than or equal to 1,000,000 reaction sites per square millimeter.

Advantageously, all the reaction sites 104 in active area 120 may be simultaneously imaged and analyzed by an optical system. In certain embodiments, active area 120 imaged and analyzed by the optical system comprises at least 12,000 reaction sites 104. In other embodiments, active area 120 imaged and analyzed by the optical system comprises at least 25,000, at least 30,000, at least 100,000, at least 1,000,000 reaction sites, or at least 10,000,000 reaction sites.

In certain embodiments, reaction sites 104 comprise a first plurality of the reaction sites characterized by a first characteristic diameter, thickness, and/or volume, and a second plurality of the reaction sites characterized by a second characteristic diameter, thickness, and/or volume that is different than that of the corresponding the first characteristic diameter, thickness, or volume. Such variation in reaction site size or dimension may be used, for example, to simultaneously analyze two or more different nucleotide sequences that may have different concentrations. Additionally or alternatively, a variation in reaction site 104 size on a single substrate 102 may be used to increase the dynamic range of a dPCR process, assay, or experiment. For example, chip 100 may comprise two or more subarrays of reaction sites 104, where each group is characterized by a diameter or thickness that is different a diameter or thickness of the reaction sites 104 of the other or remaining group(s). Each group may be sized to provide a different dynamic range of number count of a target polynucleotide. The subarrays may be located on different parts of substrate 102 or may be interspersed so that two or more subarrays extend over the entire active area of chip 100 or over a common portion of active area of chip 100.

In certain embodiments, at least some of the reaction sites 104 are tapered over all or a portion of their walls. For example, referring to FIG. 13, at least some of reaction sites 104 may comprise a chamfer 130 at surface 110. Additionally or alternatively, at least some of reaction sites 104 may comprise a chamfer 130 at surface 112 (not shown). The use of chamfered and/or tapered reaction sites have been found to reduce the average distance or total area between adjacent reaction sites 104, yet without exceeding optical limitations for minimum spacing between solution sites or test samples. As discussed above in relation to FIG. 10, a decrease in the area between adjacent reaction sites 104 may result in a reduction in the amount liquid solution that is left behind on surfaces 110, 112 during a loading process. Thus, a higher sample loading efficiency may be obtained, while still maintaining a larger effective spacing between adjacent solution sites or test samples for the optical system.

In certain embodiments, substrate 102 comprises a photostructurable material, such as certain glass or ceramic materials. In such embodiments, a method 140 shown in FIG. 14 may be used to fabricate substrate 102. Advantageously, last optional element of method 140 shown in FIG. 11 may be used to provide a substrate 102 that is opaque or nearly opaque, so that light emitted from one reaction site 104 does not enter an adjacent reaction site 104.

Method 140 may be used to provide a substrate 102 having an opacity sufficient prevent any, or nearly any, light emitted in one reaction site 104 from being transmitted into an adjacent reaction site 104. Method 140 may further comprise removing material from substrate 102 by an amount sufficient to reduce thickness between surfaces 110, 112, for example, removing material from substrate 104 by an amount sufficient to reduce the thickness between surfaces 110, 112 by at least 20 percent over an initial thickness or by at least 30 percent or 40 percent over an initial thickness. Method 140 may also include heating substrate 102 to a temperature of at least 500 degrees Celsius during fabrication. In certain embodiments, the patterned mask used in method 140 comprises a quartz plate with chrome pattern. The mask may be removed prior to exposing the at least portion of the substrate to the corrosive agent. The corrosive material used in method 140 may be hydrofluoric acid.

Figure 15:
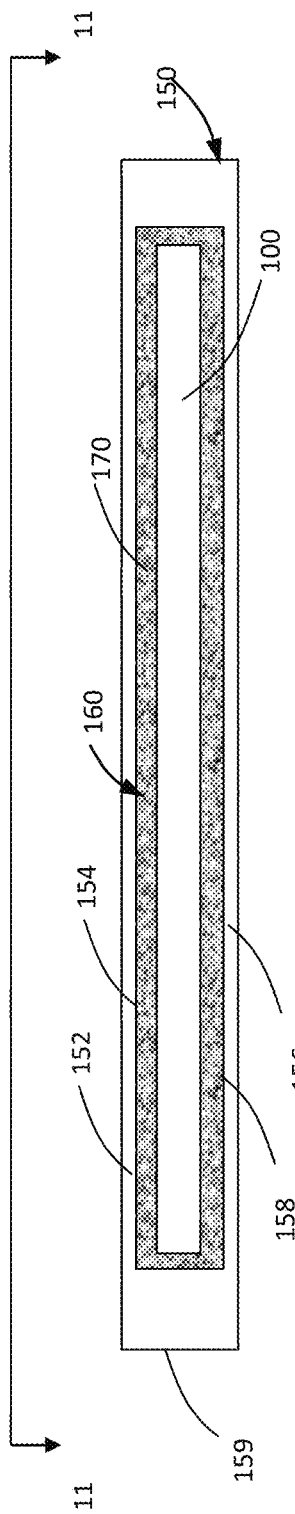
FIG. 15 illustrates an exemplary cross-section of a chip according to various embodiments described herein.
Figure 16:
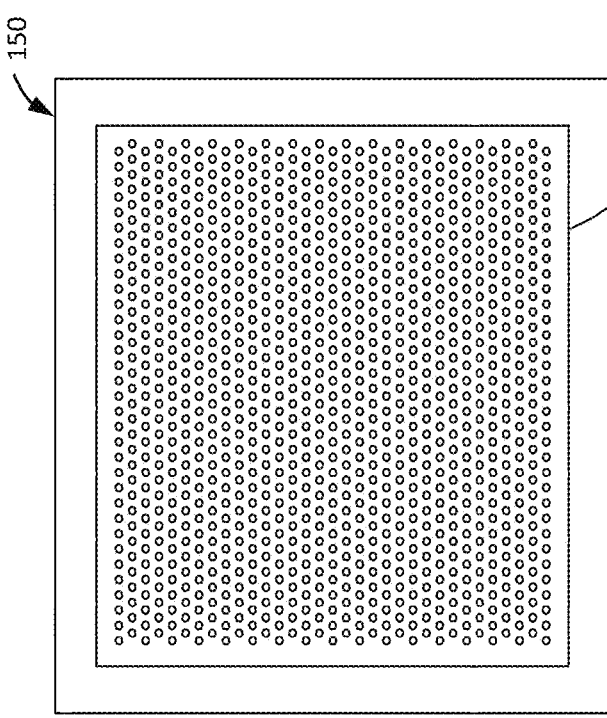
FIG. 16 illustrates an exemplary chip according to various embodiments described herein.

Referring to FIGS. 15 and 16, in certain embodiments, chip 100 is housed within a case 150 comprising first cover 152 comprising a bottom surface 154 and a second cover 156 comprising a top surface 158. Case 150 may further include one or more side walls 159 configured to maintain a spacing between the covers 152, 154. The covers 152, 154 and the walls 159 together form a cavity 160 sized to contain the chip 100. During use, chip 100 is disposed within the cavity 160 formed between surfaces 154, 158. The thickness of cavity 160 may be greater than the thickness of chip 100 such that there is a gap between chip 100 and bottom surface 154 and/or between chip 100 and top surface 158. As shown in the illustrated embodiment of FIG. 15, there may also be a gap between one or more side walls 159. Additionally or alternatively, a portion of chip 100 is attached to one or more of covers 152, 156 and one or more of side walls 159.

Case 150 may be made or formed from a metallic material, such as stainless steel, aluminum, copper, silver, or gold, or a semimetal such as graphite. Additionally or alternatively, all or portions of case 150 may be made of a non-metallic material including, but are not limited to, glass, acrylics, styrenes, polyethylenes, polycarbonates, and polypropylenes. Furthermore, case 150 may be fabricated from a range of materials that are compatible with the biological reactions, such as PCR compatible. For example, to be PCR compatible, the case may have low auto fluorescence, non-inhibiting to the PCR reaction, optically transparent to the excitation and detection wavelengths for PCR, and thermally stable at PCR temperatures.

In certain embodiments, at least one of the covers 152, 156 comprises a window configured to provide optical access to reaction sites 104. Additionally or alternatively, the entire case 150 may be made of one or more transparent or nearly transparent materials. A case related to loading of the liquid samples to the chip is described below.

Figure 17:
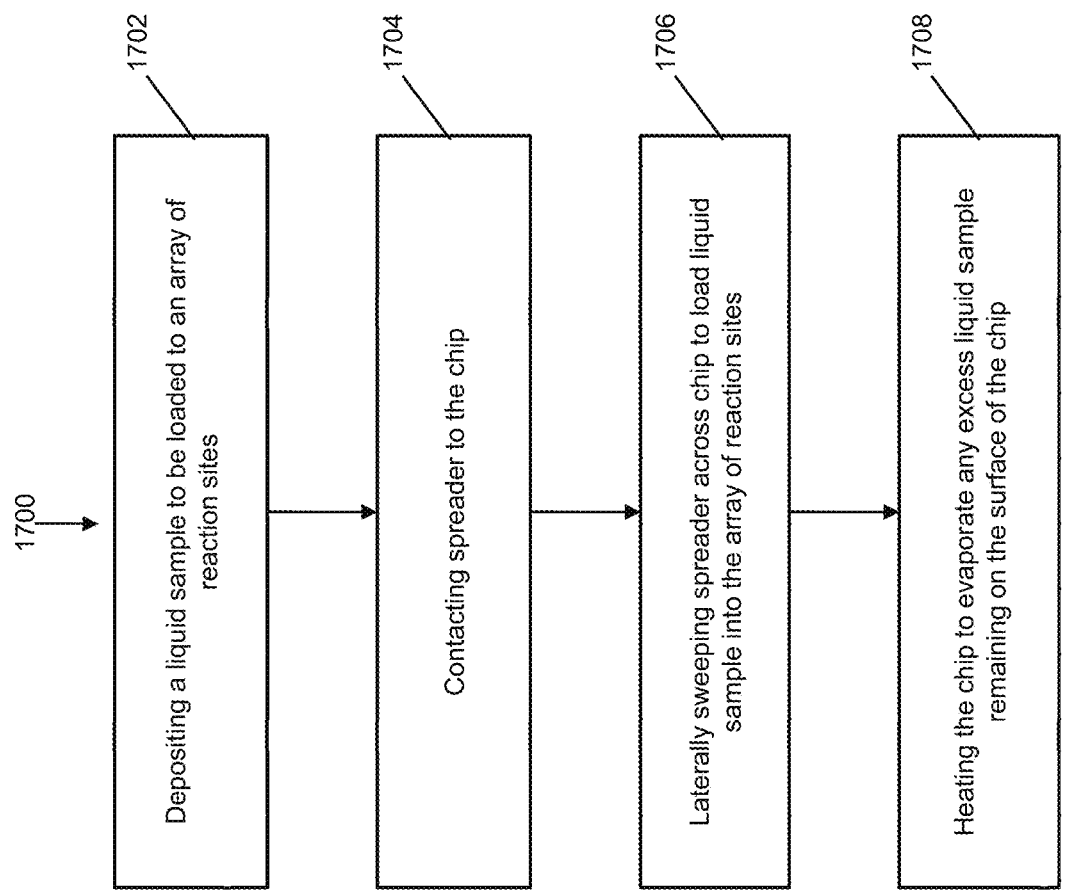
FIG. 17 illustrates a flowchart of exemplary method of loading a plurality of reaction sites in a chip according to various embodiments described herein.

According to various embodiments of the present teachings, a method for loading reaction sites in a chip is illustrated in FIG. 17. In step 1702, a liquid sample is deposited to a sample loader. In various embodiments, the sample loader may have an access port to deposit the liquid sample such that the liquid sample is held in a reservoir within the sample loader. In other embodiments, the liquid sample is deposited directly onto the chip containing the array of reaction sites. In step 1704, the sample loader is brought into contact with the chip. In step 1706, the sample loader is laterally moved across the surface of the chip such that the liquid sample is brought into contact with the reaction sites with sufficient pressure to allow the capillary action of the reaction sites to load the reaction sites with the liquid sample. Step 1708 may optionally be performed. In step 1708, removal of any excess liquid sample that was deposited on the surface of the chip by the sample loader and was not loaded into a reaction site may be facilitated by application of heat. The chip may be heated by a heating surface. Removal of excess liquid sample may help reduce errors that may occur during amplification of the biomolecules within the liquid sample, for example. Other environmental factors, such as relative humidity, may also be adjusted to allow for more efficient loading.

Figure 18:
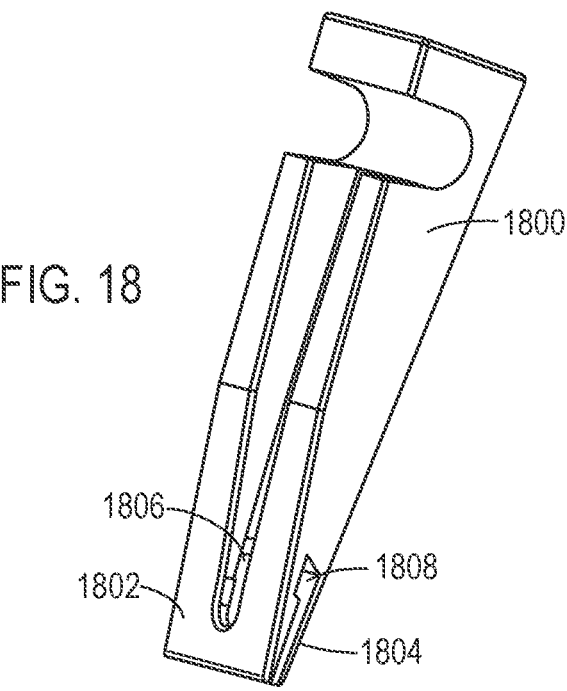
FIG. 18 illustrates a loading apparatus according to various embodiments of the present teachings.

FIG. 18 illustrates another sample loader 1800 according to various embodiments described herein. Sample loader 1800 may include a first blade 1802 and a second 1804. Sample loader 1800 may also include an access port 1806 where the liquid sample to be loaded into an array of reaction sites included in a substrate, such as a chip, may be deposited. The liquid sample deposited in access port 1806 may rest within a reservoir 1808 between first blade 1802 and second blade 1804 until the sample is loaded into the reaction sites. The liquid sample may flow within flow path 1810 to be dispensed at the end of the flow path, the tip of the sample loader 1800.

As mentioned above, sample loader 1800 may be held by a user to manually load reaction sites according to some embodiment. In other embodiments, sample loader 1800 may be installed in a loading apparatus and be used to load the reaction sites.

First blade 1802 and second blade 1804 are configured to taper toward each other so that the liquid sample wets along the edge of the width of first blade 1802 and second blade 1804. In this way, there may be even distribution of the liquid sample across the surface of the chip so that the liquid sample is efficiently loaded into the reaction sites as sample loader 1800 is swept across a chip.

Figure 19A:
FIG. 19A illustrates a side view of a sample loader according to various embodiments of the present teachings.

FIG. 19A illustrates a side view of sample loader 1800. In this view, reservoir 1808 is shown. When a liquid sample is deposited in the sample loader 1800, as described above, the liquid may rest in reservoir 1808 until the liquid sample is loaded into the reaction sites. The volume of liquid sample that may be deposited to reservoir 1808 may be 10-20 µL. In other embodiments, the volume of liquid sample loaded to the reaction sites may be from 0.5 µL to 100 µL. In yet other embodiments, the volume of liquid sample loaded to the reaction sites may be greater than 100 µL. The volume of liquid sample loaded to the reaction sites may depend on the characteristics of the material of the sample loader, the characteristics of the liquid sample, and the relationship between the sample loader and the liquid sample, as described above, for example.

Figure 19B:
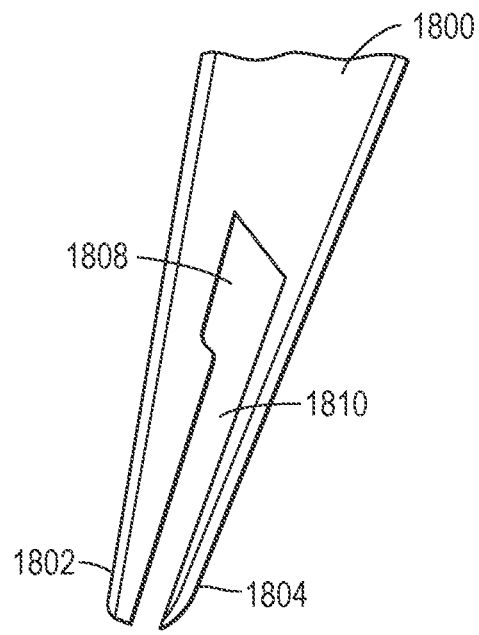
FIG. 19B illustrates an enlarged side view of a sample loader according to various embodiments of the present teachings

FIG. 19B illustrates an enlarged view of first blade 1802 and second blade 1804 of sample loader 1800. A tapering between first blade 1802 and second blade 1804 is shown. In various embodiments, the tapering angle may be from 0.1-15 degrees. In some embodiments, the tapering angle may be from 1.5-2 degrees. In various embodiments, the tapering can be so that the distance between first blade 1802 and second blade 1804 at the tip may be from 0.5 µm to 100 µm. In some embodiments, the distance between first blade 1802 and second blade 1804 may be 100 µm to 2 mm.

Further, according to various embodiments, the tip of sample loader 1800 may contact the chip at an angle of 65+/−3 degrees. According to various embodiments, the tip of sample loader 1800 may be deflected 0-0.004 inches when contacting the chip. Further the sweeping motion of sample loader 1800 across a chip may be linear. In other words, there will be minimal pitch, roll, or yaw. Spreader 1800 may move across the chip at a speed of 2-3 mm/sec, for example.

Figure 20:
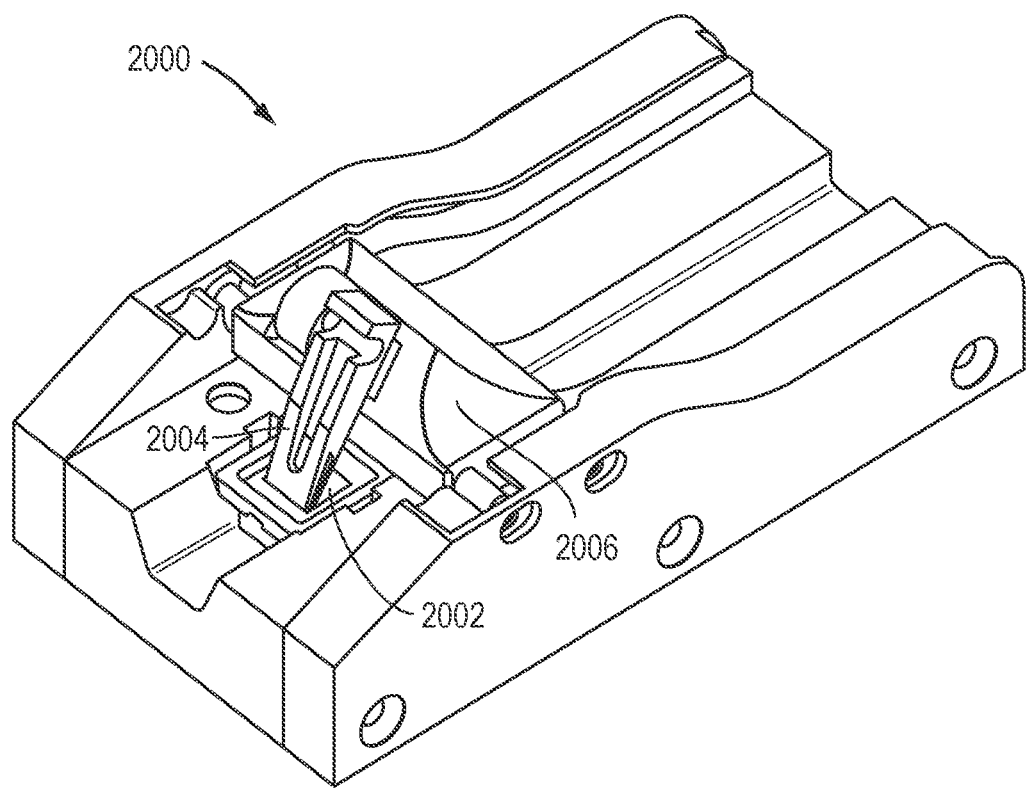
FIG. 20 illustrates a sample loader according to various embodiments described herein.

An exemplary loading apparatus 2000 is shown in FIG. 20. Loading apparatus 2000 includes a sample loader 2004 installed on a sample loader holder 2006. The sample loader holder 2006 and sample loader 2004 assembly are configured to load a liquid sample into a chip 2002 including an array of reaction sites. In various embodiments, sample loader holder 2006 may be manually moved so that sample loader 2004 is laterally moved across chip 2002 to deposit the liquid sample over chip 2002, thus loading reaction sites in chip 2002. In other embodiments, sample loader holder may be mechanically controlled by a control system to moved sample loader 2004 over chip 2002.

As described with reference to FIG. 17, the chip may be heated in some embodiments to facilitate removal of excess liquid sample. Removal of excess liquid sample may help to reduce cross contamination, or bridging, between reaction sites. In various embodiments, other environmental factors, such as relative humidity, may be adjusted to facilitate loading of the liquid sample to the reaction sites.

In various embodiments, a user may deposit the liquid sample on the chip. Then the user may hold the sample loader and laterally move the sample loader over the chip to load the liquid sample into the reaction sites. For both a manual and automated loading method, the sample loader may be positioned at an angle of 0-90 degrees to the chip while laterally moving over the chip to load the reaction sites.

It should be recognized that a sample loader, according to various embodiments described herein, may be composed of a variety of materials. For example, a sample loader may be composed of polyolefins, polyurethanes, siloxanes, or the like. In some embodiments, the sample loader may be composed of Dow 722, a low density polyethylene. However, it should be recognized that any material that will create a water contact angle of 5-179 degrees between the sample loader material and the liquid sample may be an acceptable material for the sample loader.

Liquid sample properties, sample loader material properties, and physical geometry of the sample loader along with the physical characteristics of the reaction sites and the hydrophobic/hydrophilic characteristics of the surfaces of the reaction sites as well as the chip are interactive and must all be taken into account as a complete system for the apparatus to load samples according to various embodiments of the present teachings.

The sample loader contains the liquid sample in a manner so as to distribute the liquid sample volume within the sample loader and across the width of the reaction site array included in a chip according to various embodiments. The spreading of the liquid sample from the sample loader depends on the water contact angle of the liquid sample. The water contact angle results from the relationship of the material properties of the sample loader with the properties of the liquid sample. When the water contact angle is less than 90 degrees, the relationship between the liquid sample and the substrate surface is hydrophilic and the sample exhibits a cohesive interaction with the substrate surface, which is necessary for capillary action to pull the sample into the through holes. A substrate that is too hydrophilic, for example, with a water contact angle below 50 degrees, may lead to increased pooling of excess liquid sample on the substrate surface, or inefficient loading of reaction sites, for example. Further, low contact angles may cause the liquid sample to move into some reaction sites too quickly resulting in an uneven distribution of liquid sample in the plurality of reaction sites.

Conversely when the water contact angle is over 90 degrees, the relationship between the substrate surface and the liquid sample is hydrophobic and the liquid sample will not move into the reaction sites, because the capillary force will be negative. This situation may also lead to pooling of liquid sample on the substrate surface and prevent loading of some reaction sites with liquid sample. As such, surfaces of the substrate and the reaction sites are designed to balance the hydrophobicity and hydrophilicity of the substrate and reaction sites surfaces with respect to the liquid sample.

To adjust the surface characteristics, the surfaces of the substrate and reaction sites may be coated according to embodiments described in LT00668 PCT, filed Mar. 15, 2013.

Figure 21:
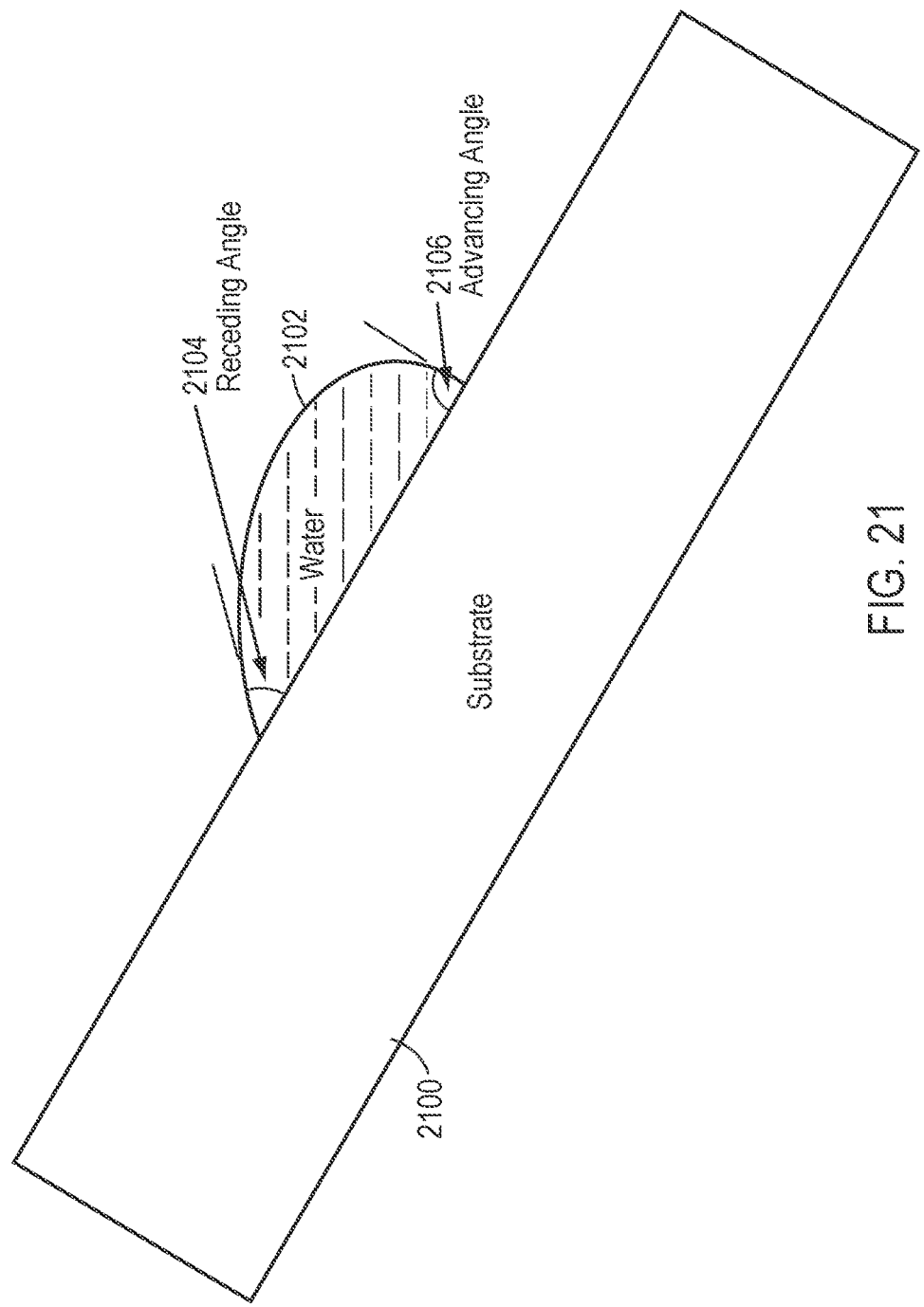
FIG. 21 illustrates a receding and advancing contact angles according to various embodiments of the present teachings.

With these characteristics in mind, according to various embodiments, efficient loading may be achieved by configuring the sample loader so that the advancing contact angle with the liquid sample is similar to the receding contact angle with the liquid sample. With reference to FIG. 21, advancing and receding contact angles are illustrated. A water droplet 2102 is shown on a substrate 2100. If the substrate is tilted, water droplet 2102 will have an advancing contact angle 2106 and a receding contact angle 2104.

According to various embodiments, the advancing contact angle is 85+/−15 degrees, and the receding contact angle is 85+/−15 degrees. According to various embodiments, a liquid sample with these contact angles readily load into the reaction sites via capillary action. The capillary action is also sufficient to contain a volume of liquid sample within the reaction site.

Figure 22:
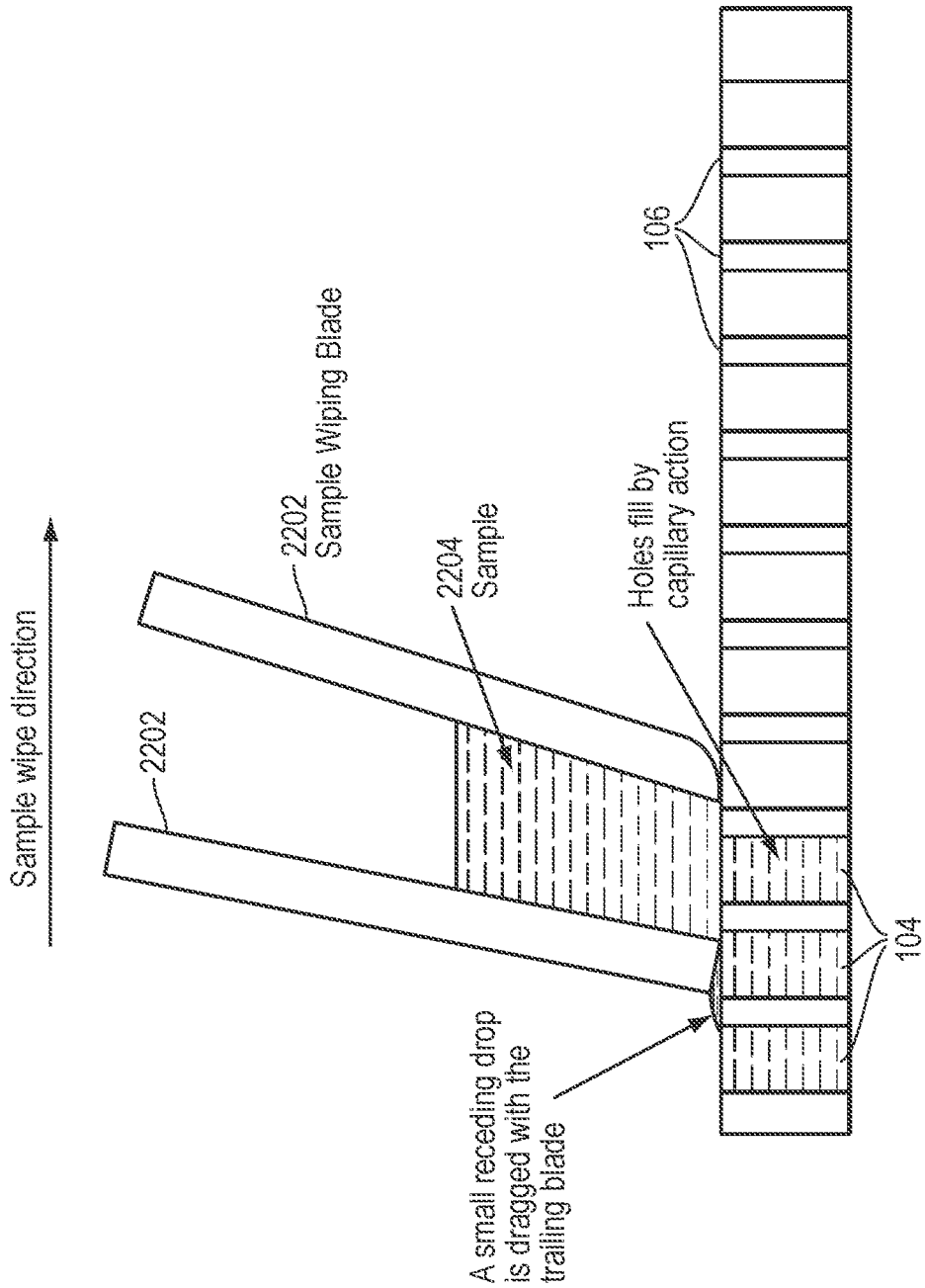
FIG. 22 illustrates loading of reaction sites by a sample loader according to various embodiments of the present teachings.

With reference to FIG. 22, loading of reaction sites by a sample loader is illustrated according to various embodiments described herein. The liquid sample 2204 to be loaded into reaction sites 104 is within sample loader 2202. Sample loader 2202 is laterally moved across surface 106. As it is moved, liquid sample 2204 is loaded into reaction sites 104 by capillary action.

The downward force of the sample loader to the chip may be dependent on the material type, sample loader thickness, and chip thickness and material. However, the downward force may range from a force to contact the chip to a force needed to break the chip. (thickness of silicon would be taken into consideration as a factor). Furthermore, in various embodiments, the sweep rate of the sample loader across the chip may be from 2.0 sec/mm up to 0.2 sec/mm.

According to various embodiments described herein for loading a chip, at least 75% of the volume of the liquid sample applied to the chip for loading is loaded into the plurality of reaction sites. In some embodiments, at least 90% of the volume of the liquid sample applied to the chip for loading is loaded into the plurality of reaction sites. In various embodiments, the volume of liquid sample applied to the chip to be loaded is equal to the volume of the sum of volumes of the plurality of reaction sites on a chip. In some embodiments, the volume of liquid sample applied to the chip is the volume of the sum of volumes of the plurality of reaction sites on the chip minus the volume of one reaction site.

Referring to FIG. 23, in certain embodiments, a carrier 2150a comprises an aperture, port, or opening 2162 that may be disposed generally perpendicular to a cover or optical access window 2152a and sized to allow passage of chip 100 into carrier 2150a. Carrier 2150a may further comprise a wiper or blade 2164 disposed along at least one long edge of opening 2162. Blade 2164 may be configured to contact or engage at least one of surfaces 110, 112 of chip 100 when chip 100 is loaded into carrier 2150a. Carrier 2150a may further comprise a film or membrane (not shown) disposed over all or a portion of opening 2162 that helps to seal cavity 2160a and is pierced when chip 100 is loaded into carrier 2150a. In certain embodiments, the membrane and blade 2164 form a single piece.

In certain embodiments, blade 2164 is configured to aid in distributing sample fluid into some or all of reaction sites 104 as chip 100 is inserted into carrier 2150a through opening 2162. For example, blade 2164 may be configured to contact one or both surfaces 110, 112 during loading of chip 100, so that liquid does not pass blade 2164, but is instead pushed, and/or pulled by capillary forces, into reaction sites 104 as surface 110, 112 moves past blade 2164. Additionally or alternatively, blade 2164 may be configured to cover one or both surfaces 110, 112 of chip 100 with a liquid, gel, or the like, for example to reduce or eliminate contamination and/or evaporation of sample fluid contained inside reaction sites 104.

Figure 24:
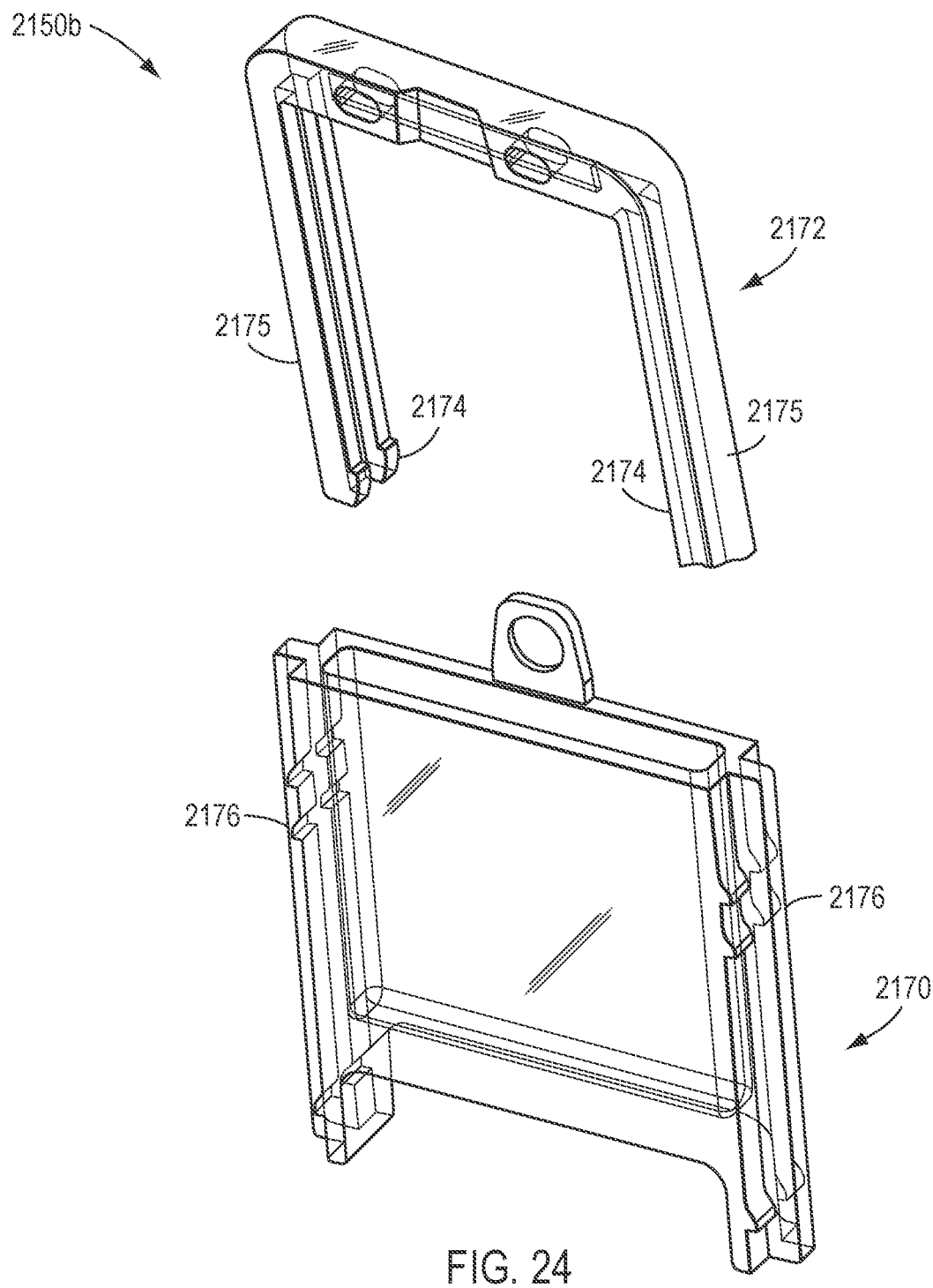
FIG. 24 illustrates a perspective view of a carrier according to various embodiments of the present teachings.

Referring to FIG. 24, in certain embodiments, a carrier 2150b comprises a body 2170, which may include some or all of the structures and features of carrier 2150a. Carrier 2150b further comprises a loader or insertion tool 2172 for holding chip 100, for aiding in loading chip 100 into a body 2170, and/or for loading a test solution into reaction sites 104. Tool 2172 may have a U-shaped body, wherein chip 100 is held inside the "U" prior to loading into body 2170. Tool 2172 may include tabs 2174 on opposite arms 2175 that are configured to engage or press into corresponding tabs or similar structure 2176 of body 2170.

Portions of cavity 2160a between chip 100 and surfaces of carrier 2150b may be filled with an immiscible fluid (e.g., a liquid or a gel material) that does not mix with test solution contained in reaction sites 104 and configured to prevent or reduce evaporation of the test solution contained from reaction sites 104. One suitable fluid for some applications is Fluorinert, sold commercially by 3M Company. However, in certain embodiments, Fluorinert may be problematic for certain PCR applications due to its propensity to readily take up air that may be later released during PCR cycling, resulting in the formation of unwanted air bubbles.

Alternatively, in certain embodiments, it has been discovered that polydimethylsiloxane (PDMS) may be used in cavity 160 if the PDMS is not fully cross-linked. In such embodiment, PDMS has been found to have several characteristics that make it suitable for use with PCR, including low auto-fluorescing, thermal stability at PCR temperatures, and being non-inhibiting to polymerization processes. In addition, PDMS may contain an aqueous sample but be gas permeable to water vapor. A typical siloxane to cross linking agent used for general applications outside embodiments of the present invention is at a ratio of 10:1 (10 percent cross-linker) by weight.

It has been discovered that by under cross-linking a PDMS material, the resulting material can function as a suitable encapsulant for reducing evaporation, while also retaining the favorable attributes discussed above and associated with the fully cross linked material. More specifically, an under cross-linked PDMS material may be formed by using less than 10 percent of the cross-linker by weight. For example, a cross link level of less than or equal to 1% by weight has been shown to meet design requirements for certain PCR applications, such as for certain dPCR applications. Multiple dPCR responses have been demonstrated using a flat plate 100 that is encapsulated with an amount of cross-linker that is less than or equal to 0.8 percent by weight. Further, due to the higher viscosity of the under cross-linked PDMS material, as compared to Fluorinert, a PDMS encapsulant may also lend itself packaging requirements and customer workflow solutions.

Figure 25:
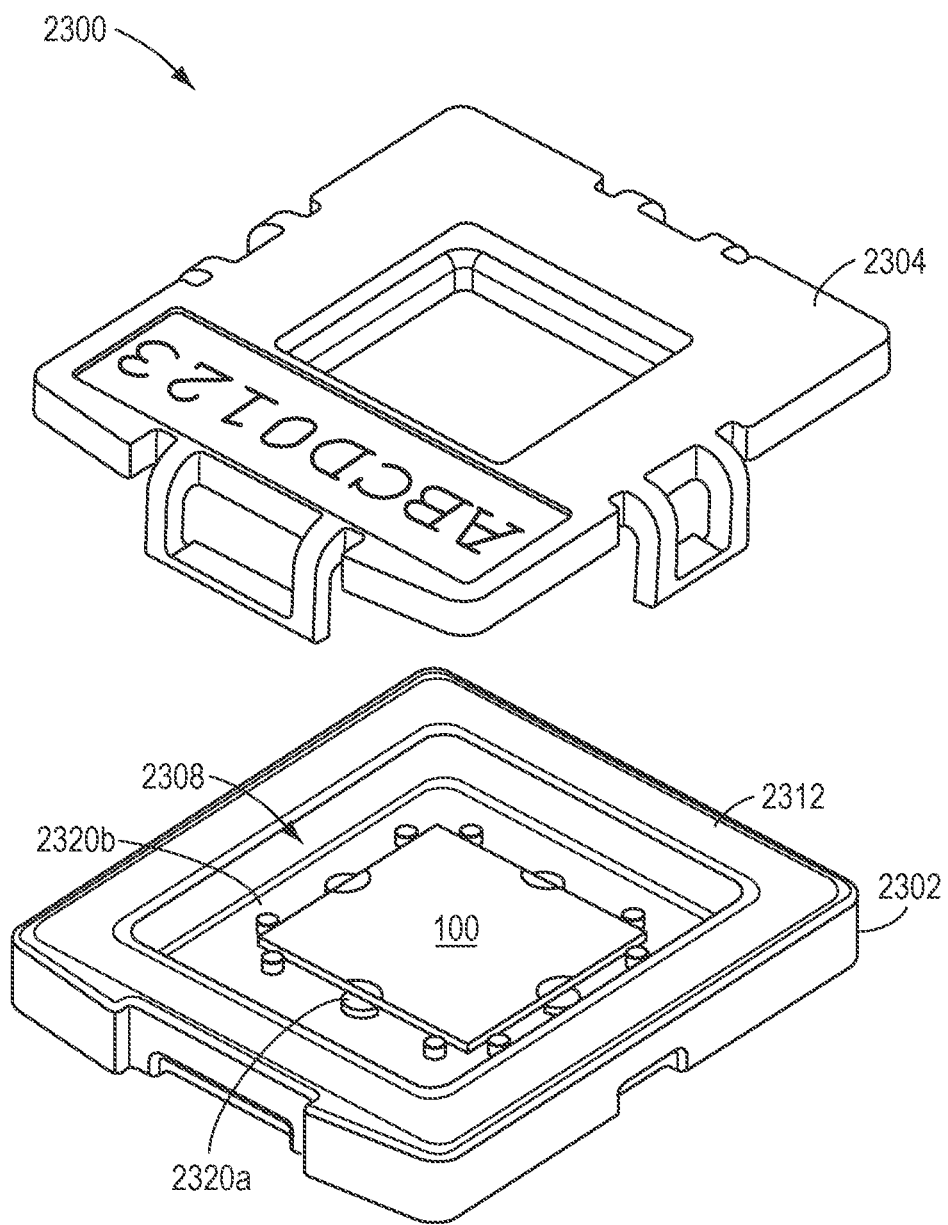
FIG. 25 illustrates a chip and associated case or holder according to various embodiments of the present teachings.

In certain embodiments, chip 100 may be configured for use in any of the enclosures, housings, or cases disclosed in U.S. provisional application No. 61/723,710, which is herein incorporated by reference in its entirety. For example, as shown in FIG. 25, chip 100 may be arranged in an enclosure, housing, or case 2300, according to an embodiment of the present invention and of provisional application No. 61/723, 710. Case 2300 may comprise a base 2302 and a cover or lid 2304 configured to sealably engage base 2302. Base 2302 and cover 2304 may be joined together to form a cavity or chamber 2308, which may receive or contain a chip 500. Chip 100 may be part of base 2302, or may be separate and/or distinct from base 2302 and be configured to be mounted or held by base 2302.

Base 2302 may comprise a plurality of bosses, tabs, staking sites, or support pads 2320 (e.g., tabs 2320a and 2320b in the illustrated embodiment) that are configured to hold and/or locate chip 100 within base 2302 and cavity 2308. One or more tabs 2382 may be staked so that material from the tab is deformed or moved to hold chip 500 firmly within base 2302. Additionally or alternatively, chip 100 may be glued to one or more tabs 182 using an adhesive, epoxy, or glue. In certain embodiments, gluing is used in conjunction with a glass or silicon chip 100 in order to avoid possible cracking or damage to such holder materials, which might be induced by use of a crimping or holding force produced by tabs 2320. In the illustrated embodiment, tabs 2320a correspond with blank regions 106 of chip 100. In certain embodiments, tabs 620a and blank regions 106 are large enough to provide proper support of chip 100, but small enough so that the active area of corresponding chip 100 provide a desired predetermined active area containing a predetermined number of reaction sites 104.

As mentioned above, a computing system may be used to control an instrument performing the biological reactions, and an instrument detecting the results of the biological reactions. Further, an automated loading apparatus may be controlled by a computing system. The computing system may be installed in the instrument, or externally connected. Further, a computing system may also be connected to an instrument over a network. An exemplary computing is illustrated in FIG. 26.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

FIG. 26 is a block diagram that illustrates a computer system 2600 that may be employed to carry out processing functionality, according to various embodiments, upon which embodiments of a thermal cycler system 500 of FIG. 5 may utilize. Computing system 2600 can include one or more processors, such as a processor 2604. Processor 2604 can be implemented using a general or special purpose processing engine such as, for example, a microprocessor, controller or other control logic. In this example, processor 2604 is connected to a bus 2602 or other communication medium.

Further, it should be appreciated that a computing system 2600 of FIG. 26 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 2600 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 2600 may include bus 2602 or other communication mechanism for communicating information, and processor 2604 coupled with bus 2602 for processing information.

Computing system 2600 also includes a memory 2606, which can be a random access memory (RAM) or other dynamic memory, coupled to bus 2602 for storing instructions to be executed by processor 2604. Memory 2606 also may be used for storing temporary variables or other intermediate information during execution of instructions to be executed by processor 2604. Computing system 2600 further includes a read only memory (ROM) 2608 or other static storage device coupled to bus 2602 for storing static information and instructions for processor 2604.

Computing system 2600 may also include a storage device 2610, such as a magnetic disk, optical disk, or solid state drive (SSD) is provided and coupled to bus 2602 for storing information and instructions. Storage device 2610 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 2610 may include other similar instrumentalities for allowing computer programs or other instructions or data to be loaded into computing system 2600. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 2610 to computing system 2600.

Computing system 2600 can also include a communications interface 2618. Communications interface 2618 can be used to allow software and data to be transferred between computing system 2600 and external devices. Examples of communications interface 2618 can include a modem, a network interface (such as an Ethernet or other NIC card), a communications port (such as for example, a USB port, a RS-232C serial port), a PCMCIA slot and card, Bluetooth, etc. Software and data transferred via communications interface 2618 are in the form of signals which can be electronic, electromagnetic, optical or other signals capable of being received by communications interface 2618. These signals may be transmitted and received by communications interface 2618 via a channel such as a wireless medium, wire or cable, fiber optics, or other communications medium. Some examples of a channel include a phone line, a cellular phone link, an RF link, a network interface, a local or wide area network, and other communications channels.

Computing system 2600 may be coupled via bus 2602 to a display 2612, such as a cathode ray tube (CRT) or liquid crystal display (LCD), for displaying information to a computer user. An input device 2614, including alphanumeric and other keys, is coupled to bus 2602 for communicating information and command selections to processor 2604, for example. An input device may also be a display, such as an LCD display, configured with touchscreen input capabilities. Another type of user input device is cursor control 2616, such as a mouse, a trackball or cursor direction keys for communicating direction information and command selections to processor 2604 and for controlling cursor movement on display 2612. This input device typically has two degrees of freedom in two axes, a first axis (e.g., x) and a second axis (e.g., y), that allows the device to specify positions in a plane. A computing system 2600 provides data processing and provides a level of confidence for such data. Consistent with certain implementations of embodiments of the present teachings, data processing and confidence values are provided by computing system 2600 in response to processor 2604 executing one or more sequences of one or more instructions contained in memory 2606. Such instructions may be read into memory 2606 from another computer-readable medium, such as storage device 2610. Execution of the sequences of instructions contained in memory 2606 causes processor 2604 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 2604 for execution. Such instructions, generally referred to as "computer program code" (which may be grouped in the form of computer programs or other groupings), when executed, enable the computing system 2600 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 2610. Volatile media includes dynamic memory, such as memory 2606. Transmission media includes coaxial cables, copper wire, and fiber optics, including the wires that comprise bus 2602.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 2604 for execution. For example, the instructions may initially be carried on magnetic disk of a remote computer. The remote computer can load the instructions into its dynamic memory and send the instructions over a telephone line using a modem. A modem local to computing system 2600 can receive the data on the telephone line and use an infra-red transmitter to convert the data to an infra-red signal. An infra-red detector coupled to bus 2602 can receive the data carried in the infra-red signal and place the data on bus 2602. Bus 2602 carries the data to memory 2606, from which processor 2604 retrieves and executes the instructions. The instructions received by memory 2606 may optionally be stored on storage device 2610 either before or after execution by processor 2604.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Exemplary systems for methods related to the various embodiments described in this document include those described in following U.S. provisional patent applications:

U.S. provisional application No. 61/612,087, filed on Mar. 6, 2012; and

U.S. provisional application No. 61/723,759, filed on Nov. 7, 2012; and

U.S. provisional application No. 61/612,005, filed on Mar. 16, 2012; and

U.S. provisional application No. 61/612,008, filed on Mar. 16, 2012; and

U.S. provisional application No. 61/723,658, filed on Nov. 7, 2012; and

U.S. provisional application No. 61/723,738, filed on Nov. 7, 2012; and

U.S. provisional application No. 61/659,029, filed on Jun. 13, 2012; and

U.S. provisional application No. 61/723,710, filed on Nov. 7, 2012; and

U.S. provisional application No. 61/774,499, filed on Mar. 7, 2013; and

PCT Application No. PCT/US2013/032002, filed Mar. 15, 2013; and

PCT Application No. PCT/US2013/032420, filed Mar. 15, 2013; and

PCT Application No. PCT/US2013/032107, filed Mar. 15, 2013; and

PCT Application No. PCT/US2013/032242, filed Mar. 15, 2013; and

PCT Application No. PCT/US2013/03189, filed Mar. 15, 2013.

All of these applications are also incorporated herein in their entirety by reference.

Although various embodiments have been described with respect to certain exemplary embodiments, examples, and applications, it will be apparent to those skilled in the art that various modifications and changes may be made without departing from the present teachings.

What is claimed is:

1. A method for performing biological reactions, the method comprising:
    configuring a chip including a substrate and a plurality of reaction sites with a coating material, wherein the coating material coats the substrate surface and each reaction site surface, the coated substrate surface has a water contact angle of 60-100 degrees, and the coated substrate surface has an advancing contact angle of 70-85 degrees;
    in a loader comprising a tip including a first blade and a second blade, depositing a liquid sample in a reservoir formed between the first blade and the second blade, wherein the tip is in fluid communication with the reservoir, and the liquid sample comprises at least one biological component or target;
    loading, with the loader, the plurality of reaction sites with the liquid sample, wherein each of the plurality of reaction sites is configured to include a volume of the liquid sample of at most one nanoliter, wherein loading further comprises contacting the tip to the chip such that the first blade and second blade of the tip are deflected;
    initiating biological reactions in the plurality of reaction sites; and
    detecting, with an optical system, a plurality of biological reactions on the chip.

2. The method of claim 1, wherein the chip includes at least 20000 reaction sites.

3. The method of claim 1, wherein the chip includes at least 30000 reaction sites.

4. The method of claim 1, wherein each reaction site of the plurality of reaction sites is a through-hole.

5. The method of claim 1, wherein each reaction site of the plurality of reaction sites is a well.

6. The method of claim 1, wherein loading includes moving the loader across the chip while contacting the first blade and the second blade to the chip to load the liquid sample from the reservoir into at least some of the plurality of reaction sites.

7. The method of claim 6, wherein the tip is deflected greater than 0 inches to less than or equal to 0.004 inches.

8. The method of claim 1, wherein the liquid sample is loaded into plurality of reaction sites via capillary action.

9. The method of claim 1, wherein each of the plurality of reaction sites is a hexagonal shape.

10. The method of claim 1, wherein the biological reactions is a polymerase chain reaction (PCR).

11. The method of claim 1, wherein the optical system includes an excitation source and an optical sensor configured to detect fluorescent signals emitted from a plurality of liquid samples within the plurality of reaction sites.

12. The method of claim 1, wherein the plurality of reaction sites includes a range of volumes to increase dynamic range.

13. The method of claim 1, further comprising:
    calculating, with a control system, a digital PCR result.

14. The method of claim 1, wherein the loading comprises:
    loading a first portion of the plurality of reaction sites with the liquid sample at a first dilution, and
    loading a second portion of the plurality of reaction sites with the liquid sample at a second dilution to increase dynamic range.

15. The method of claim 1, wherein the pitch between adjacent reaction sites is from 1 to 125 micrometers and the diameter of each reaction site is less than or equal to 75 micrometers.

16. The method of claim 1, wherein the first and second blades are comprised of a material of at least one of the following group consisting of: polyolefins, polyurethanes, and siloxane.

17. A method for loading a biological sample, the method comprising:
    configuring a chip including a substrate and a plurality of reaction sites with a coating material, wherein the coating material coats the substrate surface and each reaction site surface, the coated substrate surface has a water contact angle of 60-100 degrees, and the coated substrate surface has an advancing contact angle of 70-85 degrees;
    in a loader comprising a first blade and a second blade, depositing a liquid sample between the first blade and the second blade, the liquid sample comprising at least one biological component or target, wherein a tip includes the first blade and the second blade;
    contacting the tip of the loader with the chip such that the first blade and the second blade of the tip are deflected, wherein each of the plurality of reaction sites is configured to include a volume of the liquid sample of at most one nanoliter;
    moving the blades across the chip while contacting the first blade and the second blade to the chip; and
    while moving, loading the liquid sample into at least some of the plurality of reaction sites.

18. The method of claim 17, further comprising:
    initiating biological reactions in the plurality of reaction sites; and
    detecting, with an optical system, a plurality of biological reactions on the chip.

19. The method of claim 18, wherein the chip includes at least 20000 reaction sites.

20. The method of claim 18, wherein the chip includes at least 30000 reaction sites.

21. The method of claim 18, wherein each reaction site of the plurality of reaction sites is a through-hole.

* * * * *